(12) United States Patent
Morré et al.

(10) Patent No.: US 6,878,514 B1
(45) Date of Patent: Apr. 12, 2005

(54) METHODS FOR IDENTIFYING AGENTS THAT INHIBIT SERUM AGING FACTORS AND USES AND COMPOSITIONS THEREOF

(75) Inventors: Dorothy M. Morré, West Lafayette, IN (US); D. James Morré, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/536,551

(22) Filed: Mar. 28, 2000

Related U.S. Application Data
(60) Provisional application No. 60/126,894, filed on Mar. 30, 1999.

(51) Int. Cl.[7] .......................... C12Q 1/00; A61K 49/00; A61K 37/18; A01N 37/18
(52) U.S. Cl. .............................. 435/4; 424/9.1; 424/9.2; 514/2
(58) Field of Search .............................. 435/4; 424/9.1, 424/9.2; 514/2

(56) References Cited

U.S. PATENT DOCUMENTS

| | | | |
|---|---|---|---|
| 4,056,613 A | 11/1977 | Bertazzoli et al. | |
| 5,093,246 A | 3/1992 | Cech et al. | |
| 5,565,324 A | 10/1996 | Still et al. | |
| 5,569,673 A | * 10/1996 | Morre et al. | ................. 514/522 |
| 5,605,810 A | 2/1997 | Morréet al. | |
| 5,843,696 A | * 12/1998 | Read et al. | ..................... 435/25 |
| 6,140,063 A | * 10/2000 | Wheelock et al. | ........... 435/7.1 |
| 2001/0005719 A1 | * 6/2001 | Von Borstel | ................. 514/49 |

FOREIGN PATENT DOCUMENTS

| | | |
|---|---|---|
| WO | WO 98/33495 | 8/1998 |
| WO | WO 98/35658 | 8/1998 |
| WO | WO 98/35660 | 8/1998 |

OTHER PUBLICATIONS

Garret et al. Biochemistry. Saunders College Publishing, Harcourt Brace College Publishers, 1995, pp. 632–659.*
Aejmelaeus et al., 1997, "Ubiquinol–10 and total peroxyl radical trapping capacity of LDL lipoproteins during aging: the effects of Q–10 supplementation", Mol Aspects Med 18 Suppl:S113–20.
Andersson et al., 1994, "Modulations in hepatitic branch-point enzymes involved in isoprenoid biosynthesis upon dietary and drug treatments of rats", Biochim Biophys Acta 1214(1):79–87.
Appelkvist et al., 1994, "Regulation of coenzyme Q biosynthesis", Mol Aspects Med 15 Suppl :s37–46.
Arnheim and Cortopassi, 1992, "Deleterious mitochondrial DNA mutations accumulate in aging human tissues", Mutat Res. 275(3–6):157–67.
Arroyo et al., 1998, "Ubiquinol regeneration by plasma membrane ubiquinone reductase", Protoplasma 205:107–113.
Aruoma, 1996, "Characterization of drugs as antioxidant prophylactics", Free Rad Biol Med 20:675–705.
Austin, 1997, "Recent progress in treatment and secondary prevention of breast cancer with supplements", Alt Med Rev 2 4–11.
Balcavage and Alvager, 1982, "Reactions of malonaldehyde with mitochondrial membranes", Mech Ageing Dev.19(2):159–7.
Battino et al., 1995, "Coenyme Q content in synaptic and non–synaptic mitochondrial from different brain regions in the ageing rat", Mech Ageing Dev 78(3):173–87.
Beyer, 1994, "The role of ascorbate in antioxidant protection of biomembranes: interaction with vitamin E and coenzyme Q", J Bioenerg Biomembr 26(4):349–58.
Beyer et al., 1997, "The two–electron quinone reductase DT–diaphorase generates and maintains the antioxidant (reduced) form of coenzyme Q in membranes", Mol Aspects Med 18 Suppl:S15–23.
Beyer and Ernster, 1990, Highlights of Ubiquinone Research (Taylor & Francis, London) pp. 191–213.
Beyer et al., 1996, "The role of DT–diaphorase in the maintenance of the reduced antioxidant form of coenzyme Q in membrane systems", Proc Natl Acad Sci USA 93(6):2528–32.
Beyer et al., 1985, "Tissue coenzyme Q (ubiquinone) and protein concentrations over the life span of the laboratory rat", Mech Ageing Dev 32(2–3):267–81.
Blanchard and Hood, 1996, "Sequence to array: probing the genome's secrets", Nat Biotechnol 14(13):1649.
Boffoli et al., 1994, "Decline with age of the respiratory chain activity in human skeletal muscle", Biochim Biophys Acta, 1226(1):73–82.
Boveris et al., 1972, "The cellular production of hydrogen peroxide", Biochem J. 128(3):617–30.
Brightman et al., 1992, "A growth factor– and hormone–stimulated NADH oxidase from rat liver plasma membrane", Biochim Biophys Acta 1105(1):109–17.
Brown, 1995, "Amyotrophic lateral sclerosis: recent insights from genetics and transgenic mice", Cell 80(5):687–92.
Bruno et al., 1992, "Stimulation of NADH oxidase activity from rat liver plasma membranes by growth factors and hormones is decreased or absent with hepatoma plasma membranes", Biochem J. 284 (3):625–8.

(Continued)

Primary Examiner—Sreeni Padmanabhan
Assistant Examiner—Lauren Q. Wells
(74) Attorney, Agent, or Firm—Jones Day

(57) ABSTRACT

The invention described herein encompasses methods of preventing or treating disorders caused by oxidative damage by an aging-specific isoform of NADH oxidase (AR-NOX). The invention encompasses methods of assaying, screening, and identifying agents that inhibit AR-NOX, as well as methods using ubiquinone to inhibit the ability of AR-NOX to generate reactive oxygen species. These agents may be formulated into pharmaceutical compositions in the prevention and treatment of disorders caused by oxidative damage.

13 Claims, 5 Drawing Sheets

OTHER PUBLICATIONS

Figure 1:
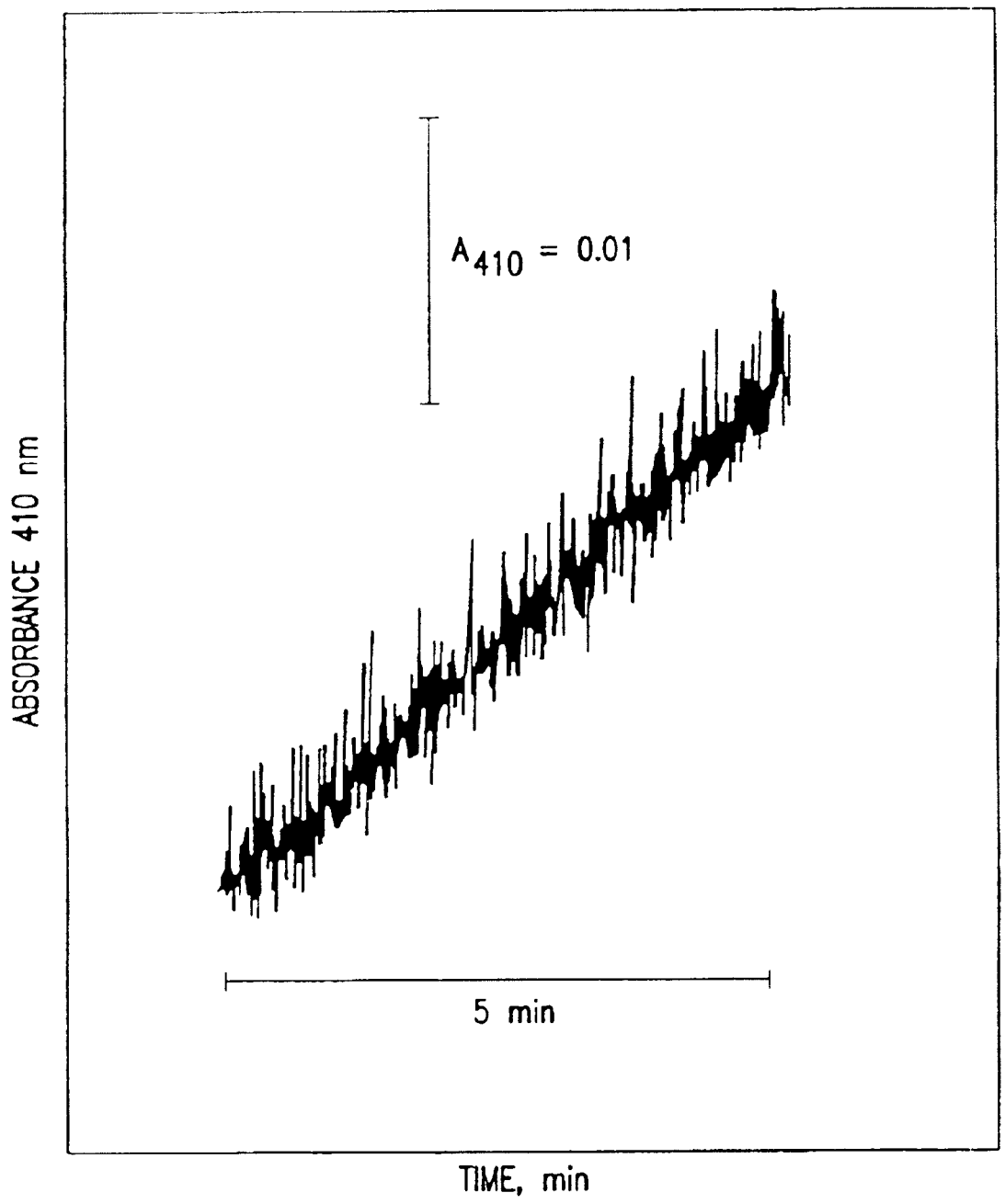

Chueh et al., 1997, "The hormone–responsive NADH oxidase of the plant plasma membrane has properties of a NADH:protein disulfide reductase", J Biol Chem 272(17):11221–7.
Chueh et al., 1997, "A 33.5–kDa heat– and protease–resistant NADH oxidase inhibited by capsaicin from sera of cancer patients", Arch Biochem Biophys 342(1):38–47.
Crane and Morré, 1977, Biomedical and Clinical Aspects of Coenzyme Q (Elsevier Scientific, New York) pp. 3–14.
Crane and Barr, 1985, Coenzyme Q (John Wiley & Sons, Chichester) pp. 1–37.
Dai et al., 1997, "Inhibition of plasma membrane NADH oxidase activity and growth of HeLa cells by natural and synthetic retinoids", Mol Cell Biochem 166(1–2):101–9.
de Grey, 1998, "Age–related oxidative stress: A mechanism proposed to explain the rise in oxidative stress during aging", J. Anti–Aging Med. 1(1):53–66.
de Grey, 1997 "A proposed refinement of the mitochondrial free radical theory of aging", Bioessays 19(2):161–6.
DeHahn et al., 1997, "NADH oxidase activity present on both the external and internal surfaces of soybean plasma membranes", Biochim Biophys Acta 1328:99–108.
Deng et al. 1993, "Amyotrophic lateral sclerosis and structural defects in Cu,Zn superoxide dismutase", Science 261(5124):1047–51.
Ernster et al., 1992, "The mode of action of lipid–soluble antioxidants in biological membranes: relationship between the effects of ubiquinol and vitamin E as inhibitors of lipid peroxidation in submitochondrial particles", Biofactors 3(4):241–8.
Ernster and Dallner, 1995, "Biochemical, physiological and medical aspects of ubiquinone function", Biochim Biophys Acta 24;1271(1):195–204.
Fields and Song, 1989, "A novel genetic system to detect protein–protein interactions", Nature 340(6230):245–6.
Gaby, 1996, "The role of Coenzyme Q10 in clinical medicine: Part I", Alt Med Rev 1:11–17.
Genova et al., 1995, "Major changes in complex I activity in mitochondria from aged rats may not be detected by direct assay of NADH:coenzyme Q reductase", Biochem J 311 (Pt 1):105–9.
Gorman et al., 1997, "Role of peroxide and superoxide anion during tumour cell apoptosis", FEBS Lett. 404(1):27–33.
Harman et al., 1972, "The biologic clock: the mitochondria?", J Am Geriatr Soc. 20(4):145–7.
Hershko, 1992, "Iron chelators in medicine", Mol Aspect Med 13(2):113–65.
Jenner, 1991, "Oxidative stress as a cause of Parkinson's disease", Acta Neurol Scand Suppl136:6–15.
Kagan et al., 1990, "Antioxidant effects of ubiquinones in microsomes and mitochondria are mediated by tocopherol recycling", Biochem Biophys Res Commun 169(3):851–7.
Kalen et al., 1990, "Uptake and metabolism of dolichol and cholesterol in perfused rat liver", Lipids 25(2):93–9.
Kalen et al., 1987, "Ubiquinone Biosynthesis by the microsomal fraction from rat liver", Biochim Biophys Acta 926(1):70–8.
Kennedy and Lyons, 1997, "Glycation, oxidation, and lipoxidation in the development of diabetic complications", Metabolism 46(12 Suppl 1):14–21.
Kishi et al., 1999, "The plasma membrane NADH oxidase of HeLa cells has hydroquinone oxidase activity", Biochim Biophys Acta 1412(1):66–77.

Larm et al., 1994, "Up–regulation of the plasma membrane oxidoreductase as a prerequisite for the viability of human Namalwa rho 0 cells", J Biol Chem 269(48):30097–100.
Lawen et al., 1994, "The universality of bioenergetic disease: the role of mitochondrial mutation and the putative inter–relationship between mitochondria and plasma membrane NADH oxidoreductase", Mol Aspects Med 15 Suppl:s13–27.
Lenaz, 1998, "Role of mitochondria in oxidative stress and ageing", Biochim Biophys Acta 1366(1–2):53–67.
Lenaz et al., 1998, "Oxidative stress, antioxidant defences and aging", Biofactors 8(3–4):195–204.
Lenaz et al., 1997, "Mitochondrial complex I defects in aging", Mol Cell Biochem. 174(1–2):329–33.
Linnane et al., 1989, "Mitochondrial DNA mutations as an important contributor to ageing and degenerative diseases", Lancet 1(8639):642–5.
Lockhart et al., 1996, "Expression monitoring by hybridization to high–density oligonucleotide arrays", Nat Biotechnol 14(13):1675–80.
Miquel, 1992, "An update on the mitochondrial–DNA mutation hypothesis of cell aging", Mutat Res. 275(3–6):209–16.
Miquel et al., 1980, "Mitochondrial role in cell aging", Exp Gerontol. 15(6):575–91.
Morré et al., 1999, "Use of dipyridyl–dithio substrates to measure directly the protein disulfide–thiol interchange activity of the auxin stimulated NADH: protein disulfide reductase (NADH oxidase) of soybean plasma membranes", Mol Cell Biochem 200(1–2):7–13.
Morré et al., 1996, "Antitumor sulfonylurea–inhibited NADH oxidase of cultured HeLa cells shed into media", Biochim Biophys Acta 1280(2):197–206.
Morré et al., 1999, "A multifunctional hydroquinone oxidase of the external cell surface and sera", Biofactors 9(2–4):179–87.
Morré, 1998, *Plasma Membrane Redox Systems and their Role in Biological Stress and Disease* (Klewer Academic Publishers, The Netherlands) pp. 121–156.
Morré et al., 1995, "Capsaicin inhibits preferentially the NADH oxidase and growth of transformed cells in culture", Proc Natl Acad Sci U S A 14;92(6):1831–5.
Morré, 1994, "Hormone– and growth factor–stimulated NADH oxidase", J Bioenerg Biomembr 26(4):421–33.
Morré et al., 1996, "Capsaicin inhibits plasma membrane NADH oxidase and growth of human and mouse melanoma lines", Eur J Cancer 32A(11):1995–2003.
Morré et al., 1995, "The antitumor sulfonylurea N–(methylphenylsulfonyl)–N'–(4–chlorophenyl) urea (LY181984) inhibits NADH oxidase activity of HeLa plasma membranes", Biochim Biophys Acta 1240(1):11–7.
Morré et al., 1997, "NADH oxidase activity from sera altered by capsaicin is widely distributed among cancer patients", Arch Biochem Biophys 342(2):224–30.
Navarro et al., 1995, "A phospholipid–dependent NADH–coenzyme Q reductase from liver plasma membrane", Biochem Biophys Res Commun 212(1):138–43.
Nohl et al., 1996, "Conditions allowing redox–cycling ubisemiquinone in mitochondria to establish a direct redox couple with molecular oxygen", Free Radic Biol Med 20(2):207–13.
Ozawa, 1995, "Mechanism of somatic mitochondrial DNA mutations associated with age and diseases", Biochim Biophys Acta 271(1):177–89.

Ozawa, 1997, "Genetic and functional changes in mitochondrial associated with aging", Physiol Rev. 77(2):425–64.

Papa and Skulachev, 1997, "Reactive oxygen species, mitochondria, apoptosis and aging", Mol Cell Biochem 174(1–2):305–19.

Pich et al., 1996, "Inhibitor sensitivity of respiratory complex I in human platelets: a possible biomarker of ageing", FEBS Lett. 380(1–2):176–8.

Richter et al., 1988, "Normal oxidative damage to mitochondrial and nuclear DNA is extensive", Proc. Natl Acad Sci U S A. 85(17):6465–7.

Rossi, 1994, "Practical ribozymes. Making ribozymes work in cells", Curr Biol 4(5):469–71.

Schena et al., 1995, "Quantitative monitoring of gene expression patterns with a complementary DNA microarray", Science 270(5235):467–70.

Schon et al., 1996, Cellular Aging and Cell Death (J. Wiley & Sons, Inc, New York) pp. 19–34.

Seddon et al., 1994, "Dietary carotenoids, vitamins A, C and E, and advanced age–related macular degeneration", JAMA 272(18):1413–20.

Shigenaga et al., 1994, "Oxidative damage and mitochondrial decay in aging", Proc Natl Acad Sci USA 91(23):10771–8.

Soderberg et al., 1990, "Lipid compositions of different regions of the human brain during aging", J Neurochem 54(2):415–23.

Steinberg, 1997, "Low density lipoprotein oxidation and its pathobiological significance", J Biol Chem. 272(34):20963–6.

Sugiyama, 1998, "HMG CoA reductase inhibitor accelerates aging effect on diaphragm mitochondrial respiratory function in rats", Biochem Mol Biol Int 46(5):923–31.

Sugiyama et al., 1993, "Changes in skeletal muscle, heart and liver mitochondrial electron transport activities in rats and dogs of various ages", Biochem Mol Biol Int. 30(5):937–44.

Syrovy and Gutmann, 1970, "Changes in speed of contraction and ATPase activity in striated muscle during old age", Exp Gerontol. 5(1):31–5.

Takahashi et al., 1995, "Reduction of ubiquinone in membrane lipids by rat liver cytosol and its involvement in the cellular defence system against lipid peroxidation", Biochem J 309 (Pt3):883–90.

Takahashi et al., 1996, "Characterization of NADPH–dependent ubiquinone reductase activity in rat liver cytosol: effect of various factors on ubiquinone–reducing activity and discrimination from other quinone reductase", J Biochem (Tokyo) 119(2):256–63.

The Merck Index, 1983, p. 9648.

Thomas et al., 1997, "Inhibition of LDL oxidation by ubiquinol–10. A protective mechanism for coenyzme Q in atherogenesis?", Mol Aspects Med 18 Suppl:S85–103.

Vailliant et al., 1996, "Effectors of the mammalian plasma membrane NADH–oxidoreductase system. Short–chain ubiquinone analogues as potent stimulators", J Bioenerg Biomembr 28(6):531–40.

Valls et al., 1994, "Protective effect of exogenous coenzyme Q against damage by adriamycin in perfused rat liver", Biochem Mol Biol Int 33(4):633–42.

Villalba et al., 1997, "Role of cytochrome b5 reductase on the antioxidant function of coenzyme Q in the plasma membrane", Mol Aspects Med 18 Suppl:S7–13.

Webb, 1999, "Is Coenzyme Q10 for real?", Prevention, Apr.:65.

Yakes and Van Houten, 1997, "Mitochondrial DNA damage is more extensive and persists longer than nuclear DNA damage in human cells following oxidative stress", Proc Natl Acad Sci USA 94(2):514–9.

Yoneda et al. 1995, "Oxygen stress induces and apoptotic cell death associated with fragmentation of mitochondrial genome", Biochem Biophys Res Commun 209(2):723–9.

Zharova and Vinogradov, 1997, "A competitive inhibition of the mitochondrial NADH–ubiquinone oxidoreductase (complex I) by ADP–ribose", Biochim Biophys Acta 1320(3):256–64.

Beers et al.: "Merck Manual of Diagnosis and Therapy" Centennial Edition, Whitehouse Station, NJ: Merck Res. Lab, US, 1999, pp. 2503–2506.

Berkow et al.: "Merck Manual of Diagnosis and Therapy" Rahway, Merck & Co., US, 1987, p. 2392.

Calvani et al.: "Mitochondrial DNA in Human Pathology" 1993, Raven Press Ltd., New York, p. 173 and pp. 180–181.

Genova et al.: "Decrease of rotenone inhibition is a sensitive parameter of complex I damage in brain non–synaptic mitochondria of aged rats." FEBS Letters, vol. 410, No. 2–3, 1997, pp. 467–469.

Kamikawa et al.: "Effects of Coenzyme Q–10 on Exercise Tolerance in Chronic Stable Angina Pectoris" American Journal of Cardiology, vol. 56, No. 4, 1985, pp. 247–251.

Mortensen et al.: "Long–term Coenzyme Q10 Therapy: A Major Advance in the Management of Resistant Myocardial Failure" Drugs Under Experimental and Clinical Research, vol. 11, No. 8, 1985, pp. 581–583.

Nagley et al.: "Mitochondrial DNA in Human Pathology" 1993, Raven Press Ltd., New York, p. 138, 142, 143, and 146.

Rowland et al.: "Coenzyme Q10 Treatment Improves the Tolerance of the Senescent Myocardium to Pacing Stress in the Rat." Cardiovascular Research, vol. 40, No. 1, Oct. 1998, pp. 165–173.

Sherratt et al.: "Mitochondrial DNA Defects: A Widening Clinical Spectrum of Disorders" Clinical Science, Biochemical Society and the Medical Research Society, London, GB, vol. 92, Mar. 1997, pp. 225–235.

Coles et al., 1996, "Coenzyme $Q_{10}$ and Lifespan Extension", Adv. AntiAging Med. 205–215.

Folkers et al., "Relevance of the Biosynthesis of Coenzyme $Q_{10}$ and of the Four bases of DNA as a Rationale for the Molecular Causes of Cancer and a Therapy", Biochem. And Biophy. Res. Commun. 224:358–361.

Hata et al., 1981, "Immunological Responsiveness of Tumor bearing Hosts 1. Effects of Coenzyme $Q_{10}$ on 20 methyl Cholanthrene Carcinogenesis", J. of the Kansai Medical University, 33(1):59–72.

Iwasa et al., 1982, "Effect of Coenzyme Q–10 and Combined Therapy of Coenzyme $Q_{10}$ and FT–207 Ftorafur For Mice Bearing Metha Tumor 2", J. of the Nat. Defense Med. College, 7(4):332–339.

Jolliet et al., 1998, "Plasmacoenzyme $Q_{10}$ concentrations in breast cancer: prognosis and therapeutic consequences", Int. J. of Clin. Pharm. And Therapeutics, 3699):506–509.

Lockwood et al., 1994, "Apparent Partial Remission of Breast Cancer in High Risk Patients Supplemented with Nutritional Antioxidants, Essential Fatty Acids and Coenzyme $Q_{10}$", Molec. Aspects Med. 15: supp 231–240.

Lockwood et al., 1995, "Progress on Therapy of Breast Cancer with Vitamin $Q_{10}$ and the Regression of Metastases", Biochem and Biophys. Res. Comm. 212(1):172–177.

Ogura et al., 1982, "Anti Oxidative Effects of Vitamin B2 Butyrate on the Cardiac Mitochondrial Disorders Induced by Adriamycin" of Nutritional Science and Vitaminology, 28(4):329–334.

Porter et al., 1978, "Synthesis, Enzyme Inhibition, and Antitumor Activity of New 1,4–Benzoquinone Analogs of Coenzyme $Q_{10}$", Bioorg. Chem. 7:333–350.

Suzuki et al., 1986, "Effects of Immunostimulation with OK 432, Coenzyme $Q_{10}$ or Levamisole on Dimethylhydrazine induced Colonic Carcinogenesis in Rats", Japanese Journal of Surgery 16(2):152–155.

* cited by examiner

US 6,878,514 B1

METHODS FOR IDENTIFYING AGENTS THAT INHIBIT SERUM AGING FACTORS AND USES AND COMPOSITIONS THEREOF

This application claims benefit of U.S. provisional application Ser. No. 60/126,894 filed Mar. 30, 1999.

1. INTRODUCTION

The present invention relates to methods for the prevention or treatment of disorders and complications of disorders resulting from cell damage caused by an aging-related isoform of NADH oxidase (AR-NOX). The invention comprises assays for screening for agents that bind AR-NOX and inhibit the ability of AR-NOX to generate reactive oxygen species as well as methods of using ubiquinone to inhibit the ability of AR-NOX to generate reactive oxygen species. The invention also encompasses using the therapeutic compounds detected in the screening assays of the invention in a pharmaceutically acceptable carrier.

2. BACKGROUND OF THE INVENTION

2.1. Mitochondrial Theory of Aging

The mitochondrial theory of aging proposes that accumulation of spontaneous somatic mutations of mitochondrial DNA (mtDNA) leads to errors of mtDNA-encoded polypeptide chains (Hannan, 1956, J. Gerontol. 11:298–300; Harman, 1972, J. Am. Geriatr. Soc. 20:145–147; Miquel et al., 1980, Exp. Gerontol. 15:575–591; Linnane et al., 1989, Lancet, I:642–645; Arnheim and Cortopassi, 1992, Mutat. Res. 275:157–167; Ozawa, 1995, Biochim. Biophys. Acta 1271:177–189; de Grey, 1997, BioEssays 19:161–166, de Grey, 1998, J. Anti-Aging Med. 1:53–66; Lenaz et al., 1997, Mol. Cell. Biochem. 174:329–333; and Lenaz et al., 1998, BioFactors 8:195–204). These errors occurring in mtDNA-encoded polypeptide chains are stochastic and randomly transmitted during mitochondrial division and cell division. The consequence of these alterations, affecting exclusively the four mitochondrial complexes involved in protein translocation, is defective oxidative phosphorylation. Respiratory chain defects may become associated with increased oxidative stress, thus establishing a vicious cycle with amplification of the original damage (Ozawa, 1995, Biochim. Biophys. Acta 1271:177–189 and Lenaz, 1998, Biochim. Biophys. Acta 1366:53–67). In this view, therefore, mutated mitochondrial DNA, despite being present only in very small quantities in the body, may be the main generator of oxidative stress. Mutations in mtDNA are mainly represented by deletions and are unevenly distributed throughout the body. Each type of deletion is usually found at a very small percentage of total mtDNA. However, considering that the total number of deletions may be several hundreds in the different copies of mtDNA, they may account for such an amount to overcome the threshold required for decreasing the respiratory chain activity (Ozawa, 1995, Biochim. Biophys. Acta 1271:177–189; Yoneda et al., 1995, Biochem. Biophys. Res. Cormn. 209:723–729; and Ozawa, 1997, Physiol. Rev. 77:425–464; Lenaz, 1998, Biochim. Biophys. Acta 1366:53–67 and Schon et al., 1996, Cellular Aging and Cell Death, J. Wiley & Sons, Inc., New York, pp. 19–34).

Aging was proposed to result from an ever-increasing level of destructive chemical reactions involving free radicals, with mitochondria as the principal mediators of the process (Harman, 1956, J. Gerontol. 11:298–300 and Harman, 1972, J. Am. Geriatr. Soc. 20:145–147). The main line of reasoning to support this idea is that, of all subcellular components, mitochondria is both a major source of free radicals and a major direct victim of free radical damage. As a result, loss of mitochondrial function may be the driving intracellular change underlying aging, and the cause of other pro-oxidant changes such as slower protein turnover. There is considerable indirect as well as direct experimental support for the theory. For example, a decline in ATP synthesis capacity and of energy-depending processes during aging has been reported (Syrovy and Gutrnann, 1997, Exp. Gerontol. 12:31–35; Sugiyama et al., 1993, Biochem. Mol. Biol. In t. 30:937–944; Boffoli et al., 1996, Biochim. Biophys. Acta 1226:73–82; and Lenaz et al., 1998, BioFactors 8:195–204).

The mitochondrial theory of aging is currently among the most popular theories of aging as it takes into account one of the most common sources of genetic lesions associated with senescence, that of mtDNA. Mitochondrial DNA is located at the inner mitochondrial membrane near the sites of formation of highly reactive oxygen species and their products. The mitochondrial genome encodes several subunits of the electron transport chain as well as components of the ATP synthase and mitochondrial tRNAs and rRNAs. Up to 2–4% of the oxygen metabolized by mitochondria is estimated to be converted to oxygen radicals because the flow process of electrons of the mitochondrial electron transport chain is not fully efficient (Boveris et al., 1972, Biochem. J. 128:617–630 and Richter et al., 1988, Proc. Natl. Acad. Sci. U.S.A. 85:6465–6467). In contrast to the nuclear genome, mtDNA may be unable to counteract the damage inflicted by those products of respiration because mitochondria lack excision and recombination repair (Miquel, 1992, Mutat. Res. 275:209–216). After an oxidative stress to cultured cells, the damage to mtDNA is higher and persists longer than that to nuclear DNA (Yakes and Van Houten, 1997, Proc. Natl. Acad. Sci. U.S.A. 94:514–519). The steady state level of mtDNA oxidative change is about ten to sixteen times greater than that of nuclear DNA as indicated by the amount of 8-oxo-2'-deoxyguanosine (a biomarker of oxidative DNA damage) formed by the reaction of hydroxyl free radicals with guanine in mtDNA compared to nuclear DNA (Richter et al., 1988, Proc. Natl. Acad. Sci. U.S.A. 85:6465–6467 and Shigenaga et al., 1994, Proc. Natl. Acad. Scd. U.S.A. 91:10771–10778). Also, lipid peroxidation of mitochondrial membranes seems to damage mtDNA as indicated by altered electrophoretic mobility (Balcavage, 1982, Mech. Aging Dev. 19:159–170).

However, alterations of mtDNA of themselves have been difficult to link to other forms of cellular and tissue changes related to aging. Chief among these is low density lipoprotein (LDL) oxidation and atherogenesis (Steinberg, 1997, J. Biol. Chem. 272:20963–20966).

2.2. Plasma Membrane Redox System

A consistent correlate of aging cells is the accumulation of somatic mutations of mitochondrial DNA (mtDNA) leading to defective oxidative phosphorylation through alterations that affect exclusively the four mitochondrial complexes involved in proton translocation (Harman, 1956, J. Gerontol. 11:298–300; Harman, 1972, J. Am. Geratr. Soc. 20:145–147; Miquel et al., 1980, Exp. Gerontol. 15:575–591; Linnane et al., 1989, Lancet I:652–645; Arnheim and Cortopassi, 1992, Mutat. Res. 275:157–167; Ozawa, 1995, Biochim. Biophys. Acta 1271:177–189; de Grey, 1997, BioEssays 19:161–166; de Grey, 1998, J. Anti-Aging Med. 1:53–66; Lenaz et al., 1997, Mol. Cell. Biochem. 174:329–333; and Lenaz et al., 1998, BioFactors 8:195–204). A major piece of the puzzle missing from our information is how mitochondrial lesions are propagated to adjacent cells and blood components in the aging cascade. A plasma membrane oxido-reductase (PMOR) system has been suggested to augment survival of mitochondrially deficient cells through regeneration of oxidized pyridine nucleotide. The pyridine nucleotide is required to sustain glycolytic ATP production in the presence of diminished respiratory chain activity (de Grey, 1997, BioEssays 19:161–166; de Grey, 1998, J. Anti-Aging Med. 1:53–66); Yoneda et al, 1995, Biochem. Biophys. Res. Comm. 209:723–729; Schon et al., 1996, Cellular Aging and Cell Death, J. Wiley and Sons, New York, pp. 19–34; Ozawa, 1997, Physiol. Rev. 77:425–464; and Lenaz, 1998, BioFactors 8:195–204).

A cell surface protein with hydroquinone (NADH) oxidase activity (designated NOX) that functions as a terminal oxidase of PMOR has been discovered by the Inventors. Thus, a complete electron transport chain involving a cytosolic hydroquinone reductase, plasma membrane located quinones and the NOX protein was elucidated by the Inventors (Kishi et al., 1999, Biochem. Biophys. Acta 1412:66–77 and Morré, 1998, Plasma Membrane Redox Systems and their Role in Biological Stress and Disease, Klewer Academic Publishers, Dordrecht, The Netherlands, pp. 121–156). This system provides a rational basis for operation of the mitochondrial theory of aging and for propagation of aging related mitochondrial lesions, including a decline in mitochondrial ATP synthetic capacity and other energy-dependent processes during aging (Boffoli et al., 1996, Biochem. Biophys. Acta 1226:73–82; Lenaz et al., 1998, BioFactors 8:195–204; de Grey, 1997, BioEssays 19:161–166; and de Grey, 1998, J. Anti-Aging Med. 1:53–66).

Alterations in mitochondria DNA are by far the most common sources of genetic lesion associated with aging and senescence. It has been widely noted that mitochondrial DNAs are located at the inner mitochondrial membrane near sites where highly reactive oxygen species and their products might be formed. Several subunits of the electron transport chain as well as components of the ATP synthase and mitochondrial tRNAs and rRNAs are encoded by the mitochondrial genome. Since the flow of electrons of the mitochondrial electron transport chain is not fully efficient, up to 2–4% of the oxygen metabolized by mitochondria has been estimated to be converted to oxygen radicals (Boveris et al., 1972, Biochem. J. 128:617–630 and Richter et al., 1988, Proc. Natl. Acad. Sci. U.S.A. 85:6465–6467). A major tenet of the mitochondrial theory of aging is that mtDNA may be unable to counteract the damage inflicted by oxygen radicals and their products due to a lack of excision and recombination repair mechanisms (Miquel, 1992, Mutat. Res. 275:209–216). This has been demonstrated in cultured cells where damage to mtDNA resulting from oxidase stress is not only higher but persists longer than does damage to nuclear DNA (Yakes and Van Houten, 1997, Proc. Natl. Acad. Sci. U.S.A. 94:514–519). Using the amount of 8-oxo-2'-deoxyguanosine as a bio-marker of oxidative DNA damage formed by the reaction of hydroxyl free radicals with guanine in mtDNA, the steady state level of mtDNA oxidative change is about 10 to 16 times greater than that of nuclear DNA (Richter et al., 1988, Proc. Natl. Acad. Sci. U.S.A. 85:6465–6467 and Shigenaga et al., 1994, Proc. Natl. Acad. Sci. U.S.A. 91:10771–10778). Even lipid peroxidation of mitochondrial membranes seems to lead to damage of mtDNA (Balcavage, 1982, Mech. Aging Dev. 19:159–170).

Nevertheless, alterations of mtDNA and other forms of cellular and tissue changes, related to aging, have been difficult to link. Chief among these is the oxidation of low density lipoproteins (LDLs) and its implications as causal to atherogenesis (Steinberg, 1997, J. Biol. Chem. 272:20963–20966).

A model to link accumulation of lesions in mtDNA to extracellular responses, such as the oxidation of lipids in low density lipoprotein (LDLs) and the attendant arterial changes, was first proposed with rho° cells (Larm et al., 1994, J. Biol. Chem. 269:30097–30100; Lawen et al., 1994, Mol. Aspects. Med. 15:s13–s27; de Grey, 1997, BioEssays 19:161–166; and de Grey, 1998, J. Anti-Aging Med. 1:53–66). These cells lack mtDNA and are unable to carry out oxidative phosphorylation. It has been demonstrated that the PMOR system actually functions to regenerate $NAD^+$ from NADH (Larm et al., 1994, J. Biol. Chem. 269:30097–30100 and Lawen et al., 1994, Mol. Aspects. Med. 15:s13–s27). In the absence of functional mitochondrial respiratory chain, NADH accumulates as the result of glycolytic production of ATP. The rho° cells lacking functional mitochondria apparently survive though enhanced electron flow to molecular oxygen via PMOR. The PMOR is accordingly over-expressed in these cells. Oxidative stress and LDL oxidation are common complicating features in diabetics (Kennedy and Lyons, 1998, Metabolism 56:14–21).

The capacity of cells to generate ATP is determined either by reoxidation of NADH by mitochondrial respiratory mechanisms (reduction of pyruvate and uridine are provided, cells can grow without a functional mitochondrial electron transfer from oxygen to water) or by cytosolic glycolytic mechanisms (reduction of pyruvate to lactate). Transformed human cells in culture provided with excess pyruvate grow anaerobically on a glucose medium where $NAD^+$ is regenerated from the NADH that is produced during glycolysis (Vaillant et al., 1996, J. Bioenerg. Biomemb. 28:531–540). This continual regeneration of $NAD^+$ ensures that the glycolytic pathway will provide sufficient ATP to sustain cell growth and viability.

2.3. Plasma Membrane Oxido-Reductase (PMOR) Chain: Role in Aging

Aging cells expressing mitochondrial lesions require a functional PMOR, as observed in rho° cells. Mitochondrial DNA encodes respiration and oxidative phosphorylation enzymes exclusively so that cells with functionally-deficient mitochondria become anaerobic if they are to survive. In such cells, the PMOR, as demonstrated by the Inventors, regenerate sufficient export of reducing equivalents to maintain the $NAD^+/NADH$ homeostasis, ensuring survival of cells completely deficient in aerobic respiration.

Work by the Inventors done in collaboration with Prof T. Kishi, Kobe-Gakuin University, Japan, has described a cell surface NADH oxidase protein, designated NOX, capable of oxidizing hydroquinones (Kishi et al., 1999, Biochem. Biophys. Acta 1412:66–77). This protein, which is located at the exterior of the cell, appears to be multifiunctional but may have a major function as a terminal oxidase of the PMOR (Morré, 1995, Biochem. Biophys. Acta 1240:201–208 and DeHahn et al., 1997, Biochem. Biophys. Acta 1328:99–108). These findings define a complete electron transfer chain of the plasma membrane capable of transfer of electrons from NADH to an external electron acceptor via a reduced quinone intermediate. The Inventors demonstrate that in cells where plasma membrane oxidoreductase (PMOR) is over-expressed/activated electrons are transferred from NADH to external acceptors via a defined electron transport chain. The resultant transfer could result subsequently in the generation of reactive oxygen species (ROS) at the cell surface. Such cell surface-generated ROS then would be capable of propagating an aging cascade originating in mitochondria to both adjacent cells as well as to circulating blood components such as low density lipoproteins.

Mammalian plasma membranes are enriched in coenzyme Q (ubiquinone) and the plasma membrane at the cytosolic surface contains a quinone reductase capable of oxidizing NADH and reducing coenzyme Q. The electron acceptor is either molecular oxygen, or under certain conditions, both molecular oxygen and protein disulfides (Morré, 1994, J. Bioenerg. Biomemb. 26:421–433; Chueh et al., 1997, J. Biol. Chem. 272:11221–11227; and Morré et al., 1998, J. Bioenerg. Biomemb. 30:477–487). The enzyme can alternate between the two acceptors (Morré, 1998, Plasma Membrane Redox Systems and their Role in Biological Stress and Disease, Kiewer Academic Publishers, Dordrecht, The Netherlands, pp. 121–156). Hormones and growth factors stimulate NADH oxidation and favor protein disulfide reduction at the expense of oxygen consumption (Brightman et al., 1992, Biochim. Biophys. Acta 1105:109–117; Morré, 1994, J. Bioenerg. Biomemb. 26:421–433; and Chueh et al., 1997, J. Biol. Chem. 272:11221–11227). Stoichiometric relationships have been demonstrated among protein disulfide reduction, NADH oxidation and protein-thiol formation using isolated plasma membranes from a plant source stimulated by an auxin plant growth factor, 2,4-D (Chuch et al., 1997, J. Biol. Chem. 272:11221–11227). A similar stoichiometry has been shown for NADH oxidation in HeLa cells (Morré et al., 1998, J. Bioenerg. Biomemb. 30:477–487).

As a terminal oxidase of the PMOR electron transport chain, the NOX protein is responsible not only for maintaining $NAD^+$/NADH homeostasis in anaerobic cells but appears to play a role in the enhanced generation of ROS in aged cells expressing mitochondrial mutations. Oxygen appears to be the principal natural electron acceptor for cytosolic NADH oxidation in the resting state. However, a number of parameters, including metals (iron or copper), could interrupt the orderly two-electron flow to molecular oxygen that ordinarily forms water and initiate a one-electron process producing superoxide ($O_2^+$) radicals (Table 3 in Section 6.2). Superoxide then initiates a reaction that generates $H_2O_2$ and other aggressive oxidants such as the hydroxy radical (OH) (Papa and Skulachev, 1997, Mol. Cell. Biochem. 174:305–319). These ROS appear to be released into the environment to react with neighboring cells and circulating molecules such as LDL (Steinberg, 1997, J. Biol. Chem. 35 272:20963–20966).

Clearly, there is a need to find agents which reduce the ability of AR-NOX to generate reactive oxygen species (ROS) for the purposes of reducing or treating the resultant physiological conditions, such as oxidation of lipids in low density lipoprotein (LDLs) and attendant arterial changes.

3. SUMMARY OF THE INVENTION

The present invention provides pharmaceutical compositions, methods of use, and pharmaceutial kits for the treatment of disorders resulting from oxidative changes in cells that result in aging by targeting an aging-related isoform of NADH oxidase (AR-NOX), shed into the sera by aging cells.

The invention is based in part, on the Inventors' discovery that ubiquinones inhibit the activity of an aging-related isoform of NADH oxidase (AR-NOX) shed into the sera by aging cells. The inhibition of AR-NOX by ubiquinones results in a decrease in the generation of reactive oxygen species by AR-NOX. A decrease in reactive oxygen species should result in a decrease of oxidative damage resulting from said reactive oxygen species.

In another embodiment, the invention comprises methods and compositions for screening assays to identify agents that sequester AR-NOX. In one embodiment, the invention encompasses methods for detecting cell-mernbrane associated AR-NOX and soluble AR-NOX in sera.

The pharmaceutical compositions further comprise varying modes of administration of compounds that sequester AR-NOX. The modes of administration of compounds includes but is not limited to capsules, tablets, soft gels, solutions, suppositories, injections, aerosols, or a kit. In yet another embodiment, the invention comprises the isolation and characterization of AR-NOX.

3.1. Definitions

As used herein, the term "disorder" refers to an ailment, disease, illness, clinical condition, or pathological condition.

As used herein, the term "reactive oxygen species" refers to oxygen derivatives from oxygen metabolism or the transfer of free electrons, resulting in the formation of free radicals (e.g., superoxides or hydroxyl radicals).

As used herein, the term "antioxidant" refers to compounds that neutralize the activity of reactive oxygen species or inhibit the cellular damage done by said reactive species.

As used herein, the term "pharmaceutically acceptable carrier" refers to a carrier medium that does not interfere with the effectiveness of the biological activity of the active ingredient, is chemically inert, and is not toxic to the patient to whom it is adminstered.

As used herein, the term "pharmaceutically acceptable derivative" refers to any homolog, analog, or fragment corresponding to the ubiquinone formulations described in Section 5.1. infra which exhibits antioxidant activity and is relatively non-toxic to the subject.

The term "therapeutic agent" refers to any molecule, compound, or treatment, preferably an antioxidant, that assists in the prevention or treatment of the disorders, or complications of disorders caused by reactive oxygen species.

The term "agent that sequesters AR-NOX" refers to any molecule, compound, or treatment that interacts with AR-NOX, thus decreasing the reaction of AR-NOX with other substrates and inhibits the ability of AR-NOX to generate reactive oxygen species.

The antioxidants, cellular components, and target proteins defined herein are abbreviated as follows:

| | |
|---|---|
| mitochondrial DNA | mtDNA |
| nicotinamide adenine dinucleotide | NADH |
| cell surface hydroquinone (NADH) oxidase with protein disulfide-thiol isomerase activity | NOX |
| NOX specific to non-cancer cells | CNOX |
| NOX specific to aged cells | AR-NOX |
| NOX specific to cancer cells | tNOX |
| low density lipoproteins | LDLs |
| plasma membrane oxido-reductase chain | PMOR |
| ubiquinone or coenzyme Q | CoQ |
| coenzyme $Q_{10}$ | $Q_{10}$ |
| reactive oxygen species | ROS |

4. BRIEF DESCRIPTION OF THE DRAWINGS

FIG. 1. Oxidation of reduced ubiquinol at 37° C. by an enzymatic preparation with NADH oxidase activity solubilized from HeLa cells by low pH treatmnent, followed by heat and proteinase K. The disappearance of reduced ubiquinol was determined from the increase in absorbance at 410 nm as a function of time in the presence of 1 mg of the HeLa protein. The concentration of quinol was 50 mM, pH 7.

Figure 2A:
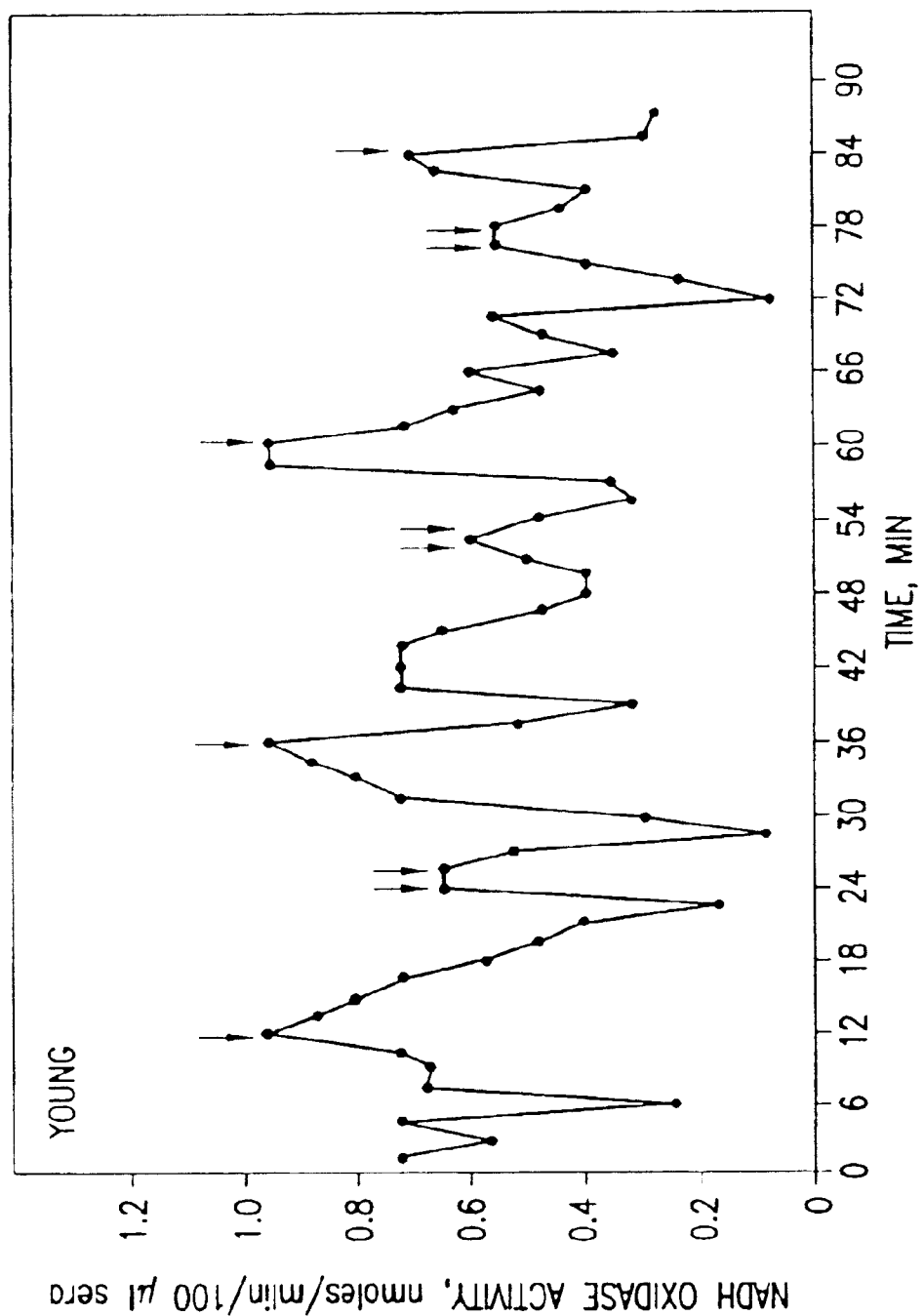
Figure 2B:
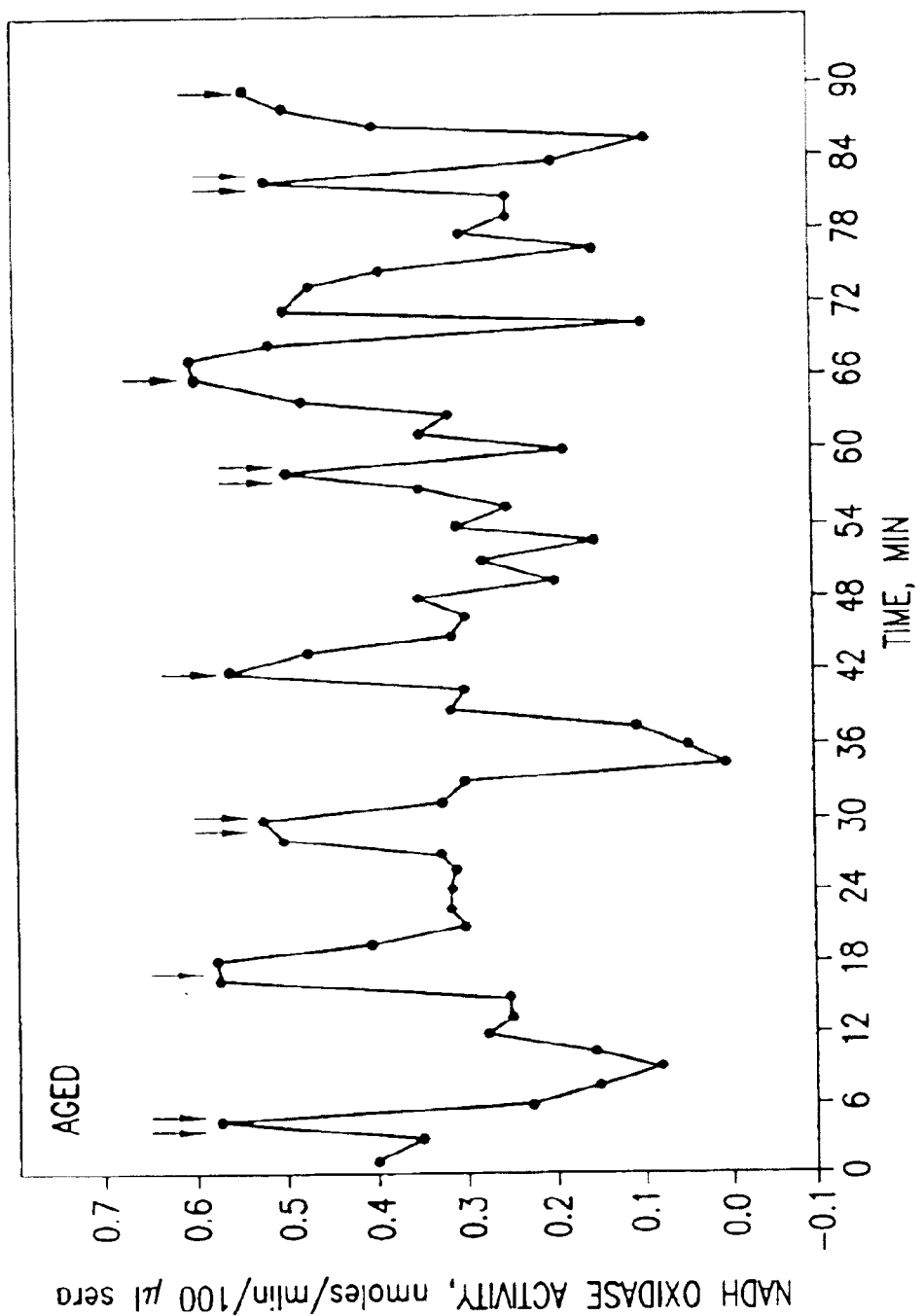
Figure 3A:
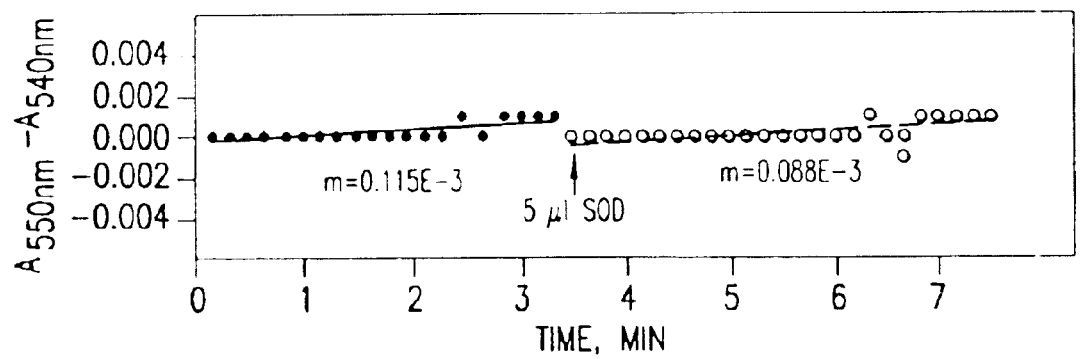
Figure 3B:
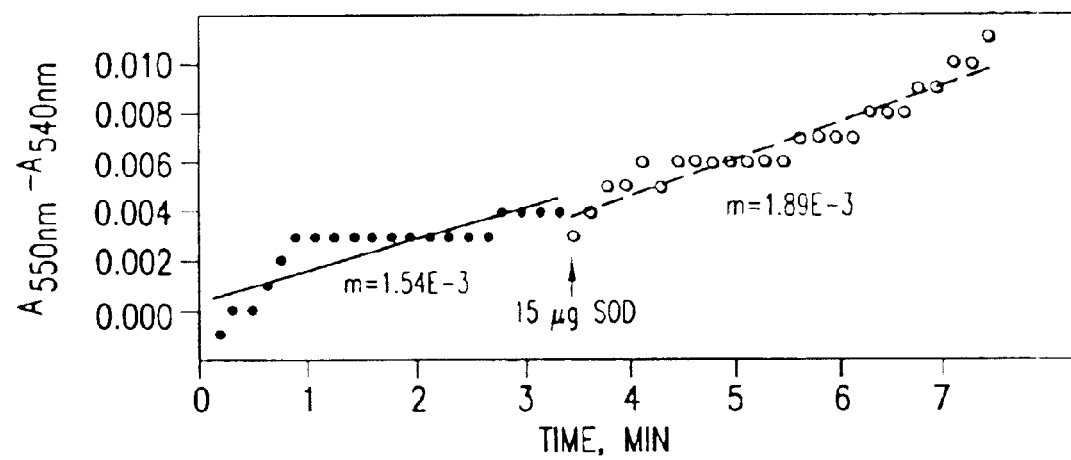
Figure 3C:
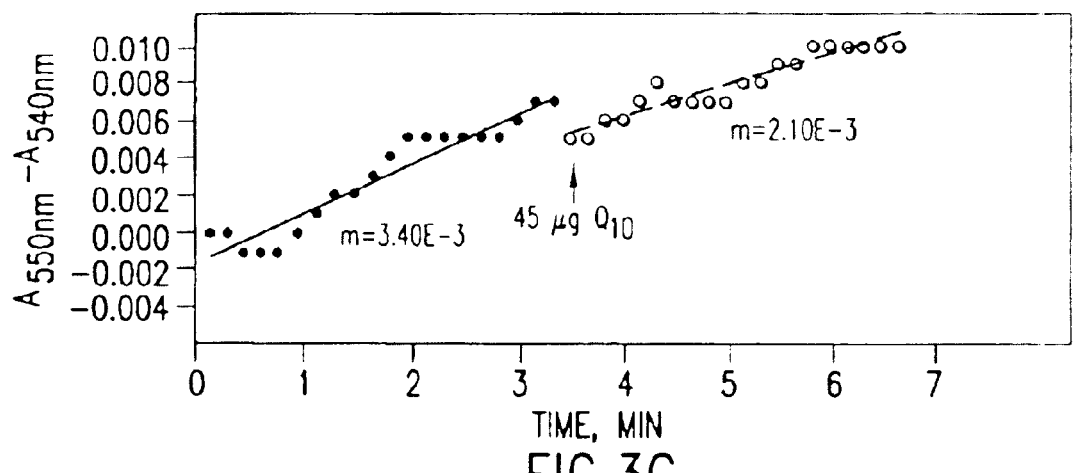
Figure 3D:
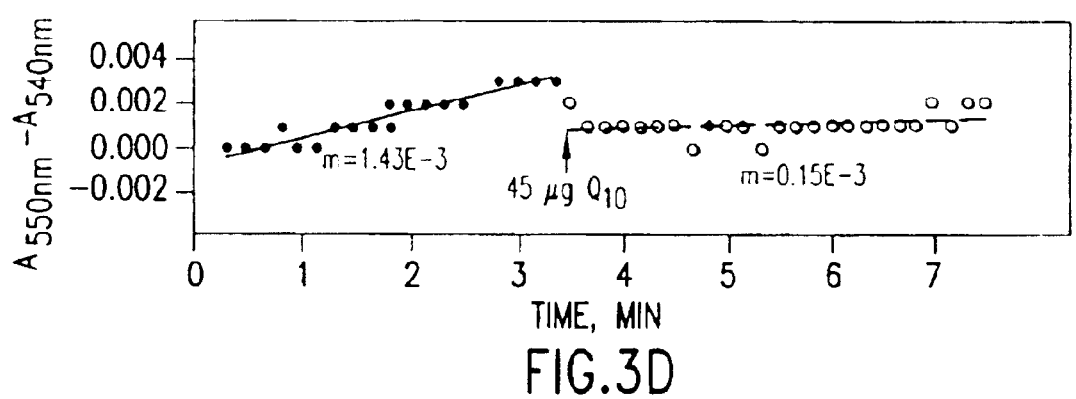

FIGS. 2A–2B. The activity of the oxidase is periodic as shown here for the oxidation of NADH by samples of sera from a young (A) and an aged (B) patient. The maxima in the time course of NADH oxidation measured as a decrease in absorbance at 340 nm over 1 minute at 1.5 minute intervals marked by single arrows have an average period length of 24 minutes and are present in all sera thus far tested. In the aged subject, which is representative of both male and female aged subjects 75 to 98, the maxima indicated by the double arrows reflect an average period length of about 26 min and are characteristic of a NOX isoform associated with aging.

FIGS. 3A–3D. Time course of cytochrome c reduction by sera determined from the $A_{550}$-$A_{540}$ determined at 10 sec intervals over 450 sec. After 200 sec either 15 mg superoxide dismutase (SOD) or 45 mg ubiquinone ($Q_{10}$) were added and the reaction was continued. A. 40 year old female±SOD. B. 98 year old female±SOD. C. 83 year old female±$Q_{10}$. D. 94 year old female±$Q_{10}$. Results from multiple patients, both male and female, are summarized in Table 4 in Section 6.2.3. Line slopes are in nmoles/min/ml sera.

5. DETAILED DESCRIPTION OF THE INVENTION

The present invention provides pharmaceutical compositions, methods of use, and pharmaceutial kits for the treatment of disorders resulting from oxidative changes in cells that result in aging by targeting an aging-related isoform of NADH oxidase (AR-NOX), shed into the sera by aging cells.

The invention is based in part, on the Inventors' discovery that ubiquinones inhibit the activity of an aging-related isoform of NADH oxidase (AR-NOX) shed into the sera by aging cells. The inhibition of this hyperactive form of NOX, AR-NOX, by ubiquinones results in a decrease in the generation of reactive oxygen species by AR-NOX. A decrease in reactive oxygen species should result in a decrease of oxidative damage resulting from said reactive oxygen species.

5.1. Plasma Membrane Hydroquinone (NADH) Oxidase (NOX)

The plasma membrane NADH oxidase (NOX) is a unique cell surface protein with hydroquinone (NADH) oxidase and protein disulfide-thiol interchange activities that normally responds to hormone- and growth factors (Brightman et al., 1992, Biochim. Biophys. Acta 1105:109–117; Morré, 1994, J. Bioenerg. Biomemb. 26:421–433, and Morré, 1998, Plasma Membrane Redox Systems and their Role in Biological Stress and Disease, Klewer Academic Publishers, Dordrecht, The Netherlands, pp. 121–156). A hormone-insensitive and drug-responsive form of the activity designated tNOX also has been described which is specific for cancer cells (Bruno et al., 1992, Biochem. J. 284:625–628; Morré and Morré, 1995, Protoplasma 184:188–195; Morré et al., 1995, Proc. Natl. Acad. Sci. U.S.A. 92:1831–1835; Morré et al., 1995, Biochim. Biophys. Acta 1240:11–17; Morré et al., 1996, Eur. J. Cancer 32A:1995–2003; Morré et al., 1997, J. Biomemb. Bioenerg. 29:269–280; and U.S. Pat. No. 5,605,810, which is incorporated by reference in its entirety for all purposes).

Because the NOX protein is located at the external plasma membrane surface and is not trarsmembrane, a functional role as an NADH oxidase is not considered likely (Morré, 1994, J. Bioenerg. Biomemb. 26:421–433; DeHahn et al., 1997, Biochem. Biophys. Acta 1328:99–108; and Morré, 1998, Plasma Membrane Redox Systems and their Role in Biological Stress and Disease, Klewer Academic Publishers, Dordrecht, The Netherlands, pp. 121–156). While the oxidation of NADH provides a basis for a convenient method to assay the activity, the ultimate electron physiological donor appears to be hydroquinones with specific activities for hydroquinone oxidation greater than or equal to that of NADH oxidation and/or protein thiol-disulfide interchange (Kishi et al., 1999, Biochem. Biophys. Acta 1412:66–77).

The NOX protein partially purified from the surface of HeLa cells also exhibits ubiquinol oxidase activity (Kishi et al., 1999, Biochem. Biophys. Acta 1412:66–77). These preparations completely lack NADH: ubiquinone reductase activity and oxidize $Q_{10}H_2$ at a rate of 3 to 6 nanoroles/min/mg protein. The $K_m$ for reduced $Q_{10}H_2$ is 30 mM. Activities are inhibited competitively by the cancer cell specific NADH oxidase inhibitors capsaicin (8-methyl-N-vanillyl-6-noneamide) and the antitumor sulfonylurea N-(4-methylphenylsulfonyl)-N'-(4-chlorophenyl)urea (LY181984) (Morré et al., 1995, Proc. Natl. Acad. Sci. U.S.A. 92:1831–1835; Morré et al., 1996, Eur. J. Cancer 32A:1995–2003; and Morré et al., 1995, Biochim. Biophys. Acta 1240:11–17). The oxidation of $Q_{10}H_2$ proceeds with what appears to be a normal two-electron transfer in keeping with the participation of the plasma membrane NADH oxidase as a terminal oxidase of plasma membrane electron transport from cytosolic NAD(P)H via coenzyme Q to acceptors at the cell surface.

Evidence that NOX proteins under certain conditions are capable of the production of ROS is presented in Table 3 in Section 6.2.2. Ultraviolet light as a source of oxidative stress in cultured cells is used to initiate superoxide generation (Morré et al., 1999, Biofactors 9:179–187). Such generation is due to the NADH oxidase because in cell lines (HeLa, human cervical carcinoma and BT-20 human mammary carcinoma), that contain a capsaicin-responsive NADH oxidase, the response to UV is inhibited by capsaicin. In the MCF10A cell line human mammary epithelia), a non-cancerous cell line lacking tNOX activity, the UV-induced generation of superoxide is unaffected by capsaicin and the resultant effects on the plasma membrane CNOX (Table 3 in Section 6.2.2). The switch whereby the oxidase may reduce oxygen by a one-electron or four-electron mechanism is not understood at present but may reside in a delicate redox balance of the carriers involved. Such a balance may be broken by oxidative stress or cell damage. Metal ions, such as iron and copper, released by tissue damage also may play a role (Hershko, 1992, Molec. Aspects Med. 13:113–165) in maintaining redox homeostasis.

5.2. Plasma Membrane Levels of Coenzyme Q

Plasma membrane ubiquinone or coenzyme Q (CoQ) plays a major role in the PMOR system. Ubiquinone or coenzyme Q (CoQ) occurs ubiquitously among tissues. In rat liver, the highest amount is found in the Golgi apparatus but it is also concentrated in the plasma membrane (Table 1) (Crane and Morré, 1977, Biomedical and Clinical Aspects of Coenzyme Q, Elsevier Scientific, Amsterdam-Oxford-New York, pp. 3–14 and Kalén et al., Lipids 25:93–99). The ubiquinone content of plasma membrane is two to five times that of microsomes and only half that of mitochondria.

TABLE 1

Distribution of ubiquinone in subcellular fractions from rat liver. The values are means ± seven experiments (Kalén et al., 1987, Biochem. Biophys. Acta 926:70–78).

| Fractions | Ubiquinone 9 (mg/mg protein) |
| --- | --- |
| Homogenate | 0.79 ± 0.08 |
| Golgi apparatus | 2.62 ± 0.15 |
| Lysosomes | 1.86 ± 0.18 |
| Mitochondria | 1.40 ± 0.16 |
| Inner mitochondrial membranes | 1.86 ± 0.13 |
| Microsomes | 0.15 ± 0.02 |
| Peroxisomes | 0.29 ± 0.04 |
| Plasma membranes | 0.74 ± 0.07 |
| Supernatant | 0.02 ± 0.004 |

Ubiquinone has long been considered to have both pro- and antioxidant roles over and above its more conventional role in mediating electron transport between NADH and succinic dehydrogenase and the cytochrome system of mitochondria (Emster and Dallner, 1995, Biochim. Biophys. Acta 127:195–204 and Crane and Barr, 1985, Coenzyme Q, John Wiley & Sons, Chichester, pp. 1–37). Both pro- and antioxidant as well as electron transport roles should be considered for ubiquinone in the plasma membrane.

CoQ is normally a product of cellular biosynthesis and provides a potentially important source of one-electron pro-oxidant oxygen reduction (Andersson et al., 1994, Biochim. Biophys. Acta 1214:79–87 and Appeikvist et al., 1994, Molec. Aspects Med. 15S:37–46). In its reduced hydroquinone form (ubiquinol), it is a powerful antioxidant acting directly upon either superoxide or indirectly on lipid radicals alone or together with vitamin E (α-tocopherol) (Crane and Barr, 1985, Coenzyme Q, John Wiley & Sons, Chichester, pp. 1–37; Beyer and Emnster, 1990, Highlights of Ubiquinone Research, Taylor & Francis, London, pp. 191–213;and Beyer, 1994, J. Bioenerg. Biomemb. 26:349–358; Kagan et al., 1990, Biochem. Biophys. Res. Comm. 169:851–857; and Ernster et al., 1992, BioFactors 3:241–248).

The antioxidant action of ubiquinol normally yields the ubisemiquinone radical. The latter is converted back to ubiquinol by re-reduction through the electron transfer chain in mitochondria or by various quinone reductases in various cellular compartrnents including the plasma membrane (Takahashi et al., 1995, Biochem. J. 309:883–890; Takahashi et al., 1996, J. Biochem. (Tokyo) 119:256–263; Beyer et al., 1996, Proc. Natl. Acad. Sci. U.S.A. 93:2528–2532; Beyer et al., 1997, Molec. Aspects Med. 18:s15–s23; Navarro et al., 1995, Biochem. Biophys. Res. Comm. 212:138–143; Villalba et al., 1995, Molec. Aspects Med. 18:s7–s13; and Arroyo et al., 1998, Protoplasma 205:107–113). Thus, ubiquinone may transform from a beneficial one-electron carrier to a superoxide generator if the ubisemiquinone anion becomes protonated (Nohl et al., 1996, Free Rad. Biol. Med. 20:207–213).

In perftised rat liver and in isolated rat hepatocytes, the anti-cancer quinone glycoside, adriamycin, induces oxidative stress by enhancing ROS production (Valls et al., 1994, Biochem. Mol. Biol. Int. 33:633–642 and Beyer et al., 1996, Proc. Natl. Acad. Sci. U.S.A. 93:2528–2532). Exogenous CoQ addition prevents this ROS production and concomitantly protects the cells from oxidative damage. Similar effects of exogenous CoQ on NOX-mediated ROS production have been observed (Table 3 in Section 6.2.2). The antioxidant effect at the plasma membrane may ameliorate LDL oxidation by scavenging ROS by PMOR produced at the cell surface (Thomas et al., 1997. Molec. Aspects Med. 18:s85–s103).

Some studies have shown that overall CoQ levels decrease with age (Beyer et al., 1985, Mech. Aging Dev. 32:267–281; Kalen et al., 1990, Lipids 25:93–99; and Genova et al., 1995, Biochem. 3.311:105–109). However this is not true for all tissues and especially for the brain, where high CoQ levels are maintained throughout aging (S öderberg et al., 1990, J. Neurochem. 54:415–423 and Battino et al., 1995, Mech. Aging Dev. 78:173–187). Thus, the invention also encompasses particular therapeutic levels of coenzyme Q for inhibiting or reducing the effects caused by overactive or aberrant cell surface PMOR system and for sequestering NOX isoforms.

5.3. Evidence for an Aging-Related CNOX Protein

The NOX protein is anchored in the outer leaflet of the plasma membrane (Morré, 1995, Biochem. Biophys. Acta 1240:201–208 and DeHahn et al., 1997, Biochem. Biophys. Acta 1328:99–108). Subsequently, the activity was shown to be shed in soluble form from the cell surface (Morré et al., 1996, Biochim. Biophys. Acta 1280:197–206). The presence of the shed form in the circulation provides an opportunity to use patient sera as a source of the NOX protein for large scale isolation and characterization studies and to examine the NOX activity in sera of subjects of advanced age in a simple and non-invasive procedure that permits side-by-side comparisons with sera of young adults. A serum form of the CNOX activity which is specific to sera from elderly subjects (AR-NOX) has been identified by the Inventors. Results are shown in Table 4 in Section 6.2.3 for elderly individuals 80–94 years of age. This sera has a superoxide-generating and aging-related enzymatic activity, which is substantially reduced by addition of 0.1 mM coenzyme Q.

The source of the circulating age-related form of the superoxide-generating activity is hypothesized to result from shedding from cells, as observed in other NOX forms. Consistent with this interpretation was the appearance of a coenzyme Q inhibitable age-related reduction of ferric cytochrome c with a buffy coat fraction (lymphocytes) comparing young and aged patients.

Thus, in one embodiment, the invention is directed to utilizing drugs which sequester, neutralize, bind, or otherwise block or eliminate, the AR-NOX protein and inhibit its ability to generate reactive oxygen species so that the cells undergo apoptosis (Morré et al., 1995, Proc. Natl. Acad. Sci. U.S.A. 92:1831–1835; Vaillant et al., 1996, J. Bioenerg. Biomemb. 28:531–540; and Dai et al., 1997, Mol. Cell. Biochem. 166:101–109). Additionally, based on the presence of an age related PMOR system capable of generating ROS at the cell surface, an approach to ablation of anaerobic cells in aged tissues is feasible. The benefits of such an approach include the fact that: (1) while normally only a small percentage of muscle fibers become anaerobic even in severely affected tissues, the elimination of these cells would not be expected to have deleterious side effects; (2) apoptosis of anaerobic cells results in the of lowering serum levels of oxidized lipoproteins and an overall reduction of the oxidative stress to surrounding healthy cells. The cells displaying all of the characteristics listed supra are hereby defined as aged cells. Generally, the characteristics of aged cells includes those that express and/or shed AR-NOX, and include, but are not limited to, those exhibiting one or more of the following characteristics: an age-related PMOR system, the ability to generate reactive oxygen species, and have functionally defective mitochondria.

In another embodiment, the invention is directed to utilizing agents, e.g., drugs or supplements, which switch the NOX protein from oxygen reduction to protein disulfide reduction. The advantage of such an approach has already been observed with plant cells in response to auxins (Chueh et al., 1997, J. Biol. Chem. 272:11221–11227).

5.4. Methods of Detecting AR-NOX

The invention further contemplates using AR-NOX as a diagnostic tool when oxidative damage to cells and/or tissue is suspected. As such, AR-NOX in tissue, cells, or circulation may be detected. In one embodiment, detection may be achieved immunologically, by employing antibodies specific to AR-NOX (described supra in Section 5.4). Said antibodies may be conjugated to a wide variety of labels, e.g., radioisotopes, enzymes, fluorescers, chemiluminescers, and the like, wherein the label provides a detectable signal.

Alternatively, in another embodiment, detection is based upon assays that recognize that sera with AR-NOX exhibits a higher rate of cytochrome c reduction than sera without AR-NOX. In this embodiment, AR-NOX reacts with a substrate capable of generating reactive oxygen species, e.g., superoxide dismutase, which results in cytochrome c reduction. The detection of cytochrome c may be detected spectrophotometrically by measuring the absorbance at about 540 nm to 550 nm.

In yet another embodiment, AR-NOX is detected in an assay which measures the disappearance of the ascorbate radical spectrophotometrically by measuring the absorbance at about 265 nm since AR-NOX reduces an electron acceptor, e.g. ascorbate radical. In another embodiment, a similar spectrophomometric assay may be carried out by measuring the reduction of $NAD^+$ by AR-NOX using methods known in the art (Morré et al., 1995, Proc. Natl. Acad. Sci. U.S.A. 92:1831–1835).

Other embodiments of the invention include assays based on the unique oscillation property of AR-NOX since NOX from healthy cells and AR-NOX exhibit varying oscillations, which are given by the oxidation of NADH, ubiquinol, or reduced vitamin $K_1$. As detailed in Section 6.2.3., varying oscillations have been observed for several NOX activity forms such that the oscillations serve as a diagnostic feature to identify NOX activity forms during their purification (Morré, 1998, Plasma Membrane Redox Systems and their Role in Biological Stress and Disease, Klewer Academic Publishers, Dordrecht, The Netherlands, pp. 121–156, which is incorporated by reference in its entirety).

In yet another embodiment of the invention, AR-NOX is detected by resistance to retinoic acid, since NOX from healthy cells is inhibited by retinoic acid and AR-NOX is not inhibited by retinoic acid (Morré, 1998, Plasma Membrane Redox Systems and their Role in Biological Stress and Disease, Klewer Academic Publishers, Dordrecht, The Netherlands, pp. 121–156).

Still other embodiments include a method using AR-NOX to identify cells where mitochondrial functions are depressed and consequently, PMOR is overexpressed. Such cells may be identified in the presence of overexpressed AR-NOX. In cells where PMOR is overexpressed as a result of decreased electron input from the respiratory chain, overcompensation by AR-NOX may represent a diagnostic feature.

AR-NOX may also be assayed for disulfide-thiol interchange activity, by using ditshio-dipyridyl substrates. Examples of derivatives of dithio-dipyridyl substrates include 2-pynmidineyione, 2,2'-ditiopyridine, and 6,6'-ditionicotinic acid, which may be used to assay the disulfide-thiol interchange activity of AR-NOX (Morré et al., 1999, Mol. Cell. Biochem. 200:7–13).

5.5. Methods of Identifying Agents that Interact with AR-NOX

The present invention relates to in vitro and in vivo methods for screening for agents which target AR-NOX. Within the broad category of in vitro selection methods, several types of methods are likely to be particularly convenient and/or useful for screening test agents. These include, but are not limited to, methods which measure a binding interaction between two or more components, and methods which measure the activity of an enzyme which is one of the interacting components, i.e., AR-NOX.

Binding interactions between two or more components can be measured in a variety of ways known in the art. One approach is to label one of the components with an easily detectable label, place it together with the other component (s) in conditions under which they would normally interact (e.g., ubiquinone), perform a separation step which separates bound labeled component from unbound labeled component, and then measure the amount of bound component. The effect of a test agent included in the binding reaction can labeling known in the art. A "detectable marker" refers to a moiety, such as a radioactive isotope or group containing same, or nonisotopic labels, such as enzymes, biotin, avidin, streptavidin, digoxygenin, luminescent agents, dyes, haptens, and the like. Luminescent agents, depending upon the source of exciting energy, can be classified as radiolurninescent, chemiluminescent, bioluminescent, and photoluminescent (including fluorescent and phosphorescent).

The separation step in this type of approach can be accomplished in various ways. In one approach, (one of) the binding partner(s) for the labeled component can be immobilized on a solid phase prior to the binding reaction, and unbound labeled component can be removed after the binding reaction by washing the solid phase. Attachment of the binding partner to the solid phase can be accomplished in various ways known to those skilled in the art, including but not limited to, chemical cross-linking, non-specific adhesion to a plastic surface, interaction with an antibody attached to the solid phase, interaction between a ligand attached to the binding partner (e.g., biotin), and a ligand-binding protein (e.g. avidin or streptavidin) attached to the solid phase.

Alternatively, the separation step can be accomplished after the labeled component has been allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner, a ligand-binding protein which can interact with a ligand previously attached to the binding partner.

Another in vitro selection method which may be used is the screening of combinatorial chemistry libraries using ubiquinone or ubiquinone derivatives as a base molecule. The methods for the generation and screening of combinatorial libraries are described in U.S. Pat. No. 5,565,324, which is incorporated by reference in its entirety. Briefly, the synthesis of the ubiquinone derivatives, using combinatorial chemistry, involves syntheses with a plurality of stages, wherein each stage involves a plurality of choices, where large numbers of products with varying compositions are obtained. The substrates carrying the final product compounds may be screen for AR-NOX binders.

Test methods which rely on measurements of AR-NOX enzymatic activity have been described in the previous subsection, supra.

The invention also comprises in vivo screening methods to identify test agents that interact with AR-NOX. In this approach, coding sequences encoding part or all of a component(s) would be introduced into a selected type of cell. Coding sequences for this approach include cloned genes, cDNAs, fragments of either, fragments amplified by the polymerase chain reaction, natural RNAs, transcribed RNAs, or the like. For example, coding sequences for two or more components which are known to interact with each other (e.g., AR-NOX and ubiquinone) are introduced into a cell, and agents are tested for their ability to moderate and/or displace the interaction between these two components.

In another embodiment, proteins that interact with AR-NOX may be identified by a yeast two-hybrid assay (Fields and Song, 1989, Nature 340:245–246). The yeast two-hybrid assay takes advantage of the properties of the GAL4 protein of the yeast *Saccharomyces cerevisiae*. GAL4 is a transcriptional activator required for the expression of genes encoding enzymes of galactose utilization, which consists of two separable and functionally essential domains: an N-terminal domain which binds to specific DNA sequences (UASG) and a C-terminal domain containing acidic regions, which is necessary to activate transcription. The two-hybrid screen comprises a system of two hybrid proteins containing parts of GAL4: the GAL4 DNA-binding domain fused to a protein 'X' and a GAL4 activating region fused to a protein 'Y'. If X and Y can form a protein-protein complex and reconstitute proximity of the GAL4 domains, transcription of a gene regulated by UASG (e.g., β-galactosidase) occurs. In this embodiment, AR-NOX may be used as the "bait" to screen for the "prey," i.e., putative interacting agents, present as cDNAs from a cDNA library. In both cases, the AR-NOX and putative interacting agents are fused in frame with the two parts of GAL4, or other transcriptional activator. Kits for two-hybrid assays are readily available, e.g., Hybrid Hunter™ Two-Hybrid system from Invitrogen.

Gene therapy approaches may also be used in accordance with the present invention to inhibit AR-NOX. Among the compounds which may interact with AR-NOX, and therefore disrupt its activity, are antisense and ribozyme molecules. Such molecules are designed to inhibit the expression of the target gene, AR-NOX. Techniques for the production and use of antisense and/or ribozyme molecules are well known to those of skill in the art and can be designed with respect to the nucleotide sequence of AR-NOX.

Antisense RNA and DNA molecules act to directly block the translation of mRNA by hybridizing to targeted mRNA and preventing protein translation. With respect to antisense DNA, oligodeoxynucleotides derived from the translation initiation site, e.g., between the −10 and +10 regions of the target gene nucleotide sequence of interest, are preferred.

Ribozymes are enzymatic RNA molecules capable of catalyzing the specific cleavage of mRNA (reviewed in Rossi, 1994, Current Biology 4:469–471). The mechanism of ribozyme action involves sequence specific hybridization of the ribozyme to complementary target RNA, followed by an endonucleolytic cleavage. The composition of ribozyme molecules must include one or more sequences complementary to the target gene mRNA, and must include the catalytic sequence responsible for mRNA cleavage (U.S. Pat. No. 5,093,246).

The invention further encompasses methods for monitoring patient response to the agents identified by the methods described supra. By monitoring circulating AR-NOX activity in patient sera, it will be possible to determine therapeutic dosages and to monitor therapeutic benefit. The response to the subject compositions may be monitored by assaying the blood or urine of the patient for the AR-NOX activity that is responsive to the agents that interact with AR-NOX. By following the above monitoring procedures, an effective dosage of the subject compositions may be administered in accordance with the requirement of the individual patient.

5.6. Inhibition of AR-NOX by Ubiquinones

The invention comprises the administration of a therapeutically effective amount of ubiquinones to a patient with a disorder or a complication of a disorder caused by oxidative damage resulting from the generation of reactive oxygen species by AR-NOX. In a preferred embodiment, the total daily amount administered is from about 1 to about 500 mg of ubiquinones. In a more preferred embodiment, the total daily amount administered is from about 1 to 100 mg of ubiquinones.

The invention is based on studies by the Inventors that have identified a serum form of AR-NOX which is specific to sera from elderly patients, and absent from sera of younger patients. Not only is there a superoxide-generating and aging-related enzymatic activity present in sera of the elderly patients, but also, the aging-related enzymatic activity is reduced by the addition of ubiquinone.

In one embodiment, the invention is used to identify patients suffering from disorders associated with reactive oxygen species who may be responsive to treatment with ubiquinones. Such responsive patients may be identified by assay of serum or urine for ubiquinone responsive superoxide generation. The generation of superoxide may be followed by reduction of cytochrome c (described in Section 6.1.3) or any other suitable biological or chemical method.

The ubiquinones are benzoquinones with a base structure of 2,3dimethoxy-s-methylbenzoquinone nucleus ("$Q_n$") and differ in the number of carbon atoms in the side chain of the 6-position, wherein n is the number of carbon units in the side chain (n is 1 to 12). The differences in properties are due to the difference in length of the side chain (Merck Index 10$^{th}$ Edition, 1983, Merck & Co., Inc., Rahway, N.J., p. 1407). Naturally occurring derivatives of ubiquinone are the coenzymes $Q_6$ to $Q_{10}$ wherein $Q_{10}$, is naturally occurring in humans and $Q_9$ is naturally occurring in rats.

The invention comprises a treating a patient with a pharmacologically effective amount of ubiquinones to inhibit the generation of reactive oxygen species. In a preferred embodiment, the ubiquinones are of the human derivative $Q_{10}$. In another embodiment the ubiquinones comprise the naturally occurring derivatives $Q_6$, $Q_7$, $Q_8$, and $Q_9$. In another embodiment, the ubiquinones comprise other derivatives $Q_1$, $Q_2$, $Q_3$, $Q_4$, $Q_5$, $Q_{11}$, and $Q_{12}$. In another embodiment, the invention comprises mixtures of the ubiquinone derivatives described supra. The invention further comprises all pharmaceutically acceptable derivatives of the compositions listed supra for methods of treating a patient with an AR-NOX related disorder, with ubiquinone administration in the range of 0.1 to 100 mg per kg body weight.

In addition, the invention provides a method for screening for test compounds that interact with AR-NOX further comprising comparing the interaction of AR-NOX of the test compound to the interaction of AR-NOX with ubiquinone, wherein the interaction of AR-NOX with ubiquinone serves as a positive control.

The invention also encompasses methods for monitoring patient response to ubiquinones. By monitoring circulating AR-NOX activity in patient sera, it will be possible to determine therapeutic dosages and to monitor therapeutic benefit from ubiquinones. The response to the subject compositions may be monitored by assaying the blood or urine of the patient for the AR-NOX activity that is responsive to the ubiquinone compositions. By following the above monitoring procedures, an effective dosage of the subject compositions may be administered in accordance with the requirement of the individual patient.

5.7. Isolation and Characterization of AR-NOX

The AR-NOX protein has been purified by the Inventors from lymphocytes and sera from aged individuals. The AR-NOX protein was purified by standard protein preparative techniques well known to those skilled in the art including ammonium sulfate precipitation, anion exchange, gel filtration, preparative SDS-PAGE and hydrophobic interaction chromatography, HPLC, and FPLC (Morré et al., 1996, Biochem. Biophys. Acta 1280)197–206 and Current Protocols in Molecular Biology, Green Publishing Associates and Wiley Intersciences, N.Y.). The ability to generate superoxide as evidenced by reduction of cytochrome c and inhibition by coenzyme Q were used as selection criteria Sufficient AR-NOX amino acid sequence was obtained by the Inventors to generate degenerate oligonucleotide primers for the amplification of a portion of the AR-NOX nucleic acid sequence.

The Inventors have also generated a NOX-specific polyclonal antibody to the AR-NOX protein from lymphocytes. Once the amino acid sequence of AR-NOX is deduced from the corresponding cDNA sequence, the amino acid sequence may be used to strategically generate peptide sera with therapeutic potential as probes specific to AR-NOX to investigate and ameliorate NOX responses to aging. Three criteria of the known protein sequence may be used in selecting sequences for antibody production: 1. hydrophilicity as calculated according to the algorithm of Hopp and Woods (Hopp and Woods 1981, Proc. Natl. Acad. Sci. U.S.A. 78:3824–3828); 2, surface probability as calculated according to the formula of Emini et al. (Emini et al., 1985, J. Virol. 53:836–839); and 3. the antigenic index measuring the probability that a region is antigenic as calculated by summing several weighted measures of secondary structure (Jamieson and Wolf, 1988, CABIOS 4:181–186). Peptide antibodies can be affinity-purified using immobilized peptide. The peptide antisera may be employed in co-incubation experiments with isolated lymphocytes from aged individuals and isolated lipoprotein particles to demonstrate that specific AR-NOX inhibition can ablate propagation of oxidative stress in both in vitro and in vivo systems.

The present invention also relates to methods for cloning of AR-NOX. Using methods which are well known to those skilled in the art, recombinant cDNA libraries may be constructed using RNA prepared from cells known to express AR-NOX. The cDNA libraries may be constructed using a variety of vector systems, including but not limited to, bacteriophage vectors, plasmid vectors or mammalian expression vectors. See, for example, the techniques described in Sambrook et al., 1989, Molecular Cloning: A Laboratory Manual, Cold Spring Harbor Laboratory, N.Y. and Current Protocols in Molecular Biology, Green Publishing Associates and Wiley Intersciences, N.Y. Alternatively, a human cDNA library library may be obtained from a commercial source, e.g. Stratagene.

The recombinant cDNA libraries may be screened using a number of different techniques which are well known to those skilled in the art. For example, a mixture of degenerate oligonucleotide probes may be designed utilizing the partial amino acid sequence of AR-NOX. The oligonucleotides may be labeled and used directly to screen a cDNA library for clones containing inserts with sequence homology to the oligonucleotide sequences. Alternatively, the oligonucleotides may be used as primers in a polymerase chain reaction. The template for the reaction is cDNA may be obtained by reverse transcription of mRNA prepared from cells known to express AR-NOX, ie., lymphocytes from aged individuals. Alternatively, the template may be cDNA from a human cDNA library library obtained from a commercial source, e.g., Stratagene. The amplified DNA fragment may be labeled and used to screen a library for isolation of full length clones. In another example, an expression library may be immunologically screened using antibodies directed against AR-NOX. In yet another embodiment of the invention, a cDNA library may be engineered into a mammalian expression vector and screened by transfection into the appropriate mammalian cell line followed by assaying for AR-NOX activity in the tissue culture supernatant.

In yet another embodiment of the invention, a method for cloning AR-NOX by means of polymerase chain reaction may be used to clone a cDNA coding for AR-NOX. Such a method may be utilized using RNA prepared from lymphocytes of aged individuals. Alternatively, AR-NOX may be cloned by polymerase chain reaction amplification of a human cDNA library obtained from a commercial source (e.g., Stratagene).

In addition, gene expression assays using gene expression arrays or microarrays are now practicable for identifying changes in gene expression patterns between different cells or tissue types (see, e.g., Schena et al., 1995, Science 270:467–470; Lockhart et al., 1996, Nature Biotechnology 14:1674–1680; and Blanchard et al., 1996, Nature Biotechnology 14:1649). Thus, in another, alternative embodiment of the invention, such gene expression arrays or microarrays may be used to compare mRNA expression patterns in cells that exhibit AR-NOX activity (e.g., as determined by one of the assays of the present invention) to mRNA expression patterns in cells that do not exhibit AR-NOX activity and thus, do not express AR-NOX.

5.8. Target Disorders

Disorders that can be treated by the methods of the present invention include any clinical condition in which oxidative species have been implicated.

Examples of clinical conditions in which oxidative species have been implicated include, but are not limited to, ischemia-reperfusion injury (e.g., stroke/myocardial infarction and organ transplantation), cancer, aging, arthritis associated with age, fatigue associated with age, alcoholism, red blood cell defects (e.g., favism, malaria, sickle cell anemia, Fanconi's anemia, and protoporphyrin photo-oxidation), iron overload (e.g., nutritional deficiencies, Kwashiorkor, thalassemia, dietary iron overload, idiopathic hemochromatosis), kidney (e.g., metal ion-mediated nephrotoxicity, aminoglycoside nephrotoxicity, and autoimmune nephrotic syndromes), gastrointestinal tract (e.g., oral iron poisoning, endotoxin liver injury, free fatty acid-induced pancreatitis, nonsteroidal antiinflammatory drug induced gastrointestinal tract lesions, and diabetogenic actions of alloxan), inflammatory-immune injury (e.g., rheumatoid arthritis, glomerulonephritis, autoimmune diseases, vasculitis, and hepatitis B virus), brain (e.g., Parkinson's disease, neurotoxins, allergic encephalomyelitis, potentiation of traumatic injury, hypertensive cerebrovascular injury, and vitamin E deficiency), heart and cardiovascular system (e.g., atherosclerosis, adriamnycin cardiotoxicity, Keshan disease (selenium deficiency) and alcohol cardiomyopathy, eye (e.g., photic retinopathy, occular hemorrhage, cataractogenesis, and degenerative retinal damange), amyotrophic lateral sclerosis, and age-related macular degeneration (Slater, 1989, Free Rad. Res. Comm. 7:119–390; Deng et al., 1993, Science 261:1047–1051; Seddon et al., 1994, JAMA 272:1413–1420; Brown, 1995, Cell 80:687–692; and Jenner, 1991, Acta Neurol. Scand. 84:6–15).

The invention is also directed to preventing or alleviating complications of diabetes, atherogenesis, atherosclerosis, and related diseases. Oxidative stress and LDL oxidation are common complicating features in diabetics and circulating AR-NOX offers opportunities for redox modulation of blood constituents important to aging, atherogenesis, and atherosclerosis (Kennedy and Lyons, 1998, Metabolism 56;14–21).

In one embodiment, the invention is directed towards a method of preventing a complication of a primary disorder in patients wherein said complication results from oxidative damage resulting from the generation of reactive oxygen species by AR-NOX. The method comprises administering to a patient with a primary disorder, in an amount effective to prevent said complication, an agent or agents that sequesters AR-NOX, in a pharmaceutically acceptable carrier.

In another embodiment, the invention is directed towards a method of preventing a secondary disorder in patients having a primary disorder that causes oxidative damage resulting from the generation of reactive oxygen species by AR-NOX. The method comprises administering to a patient having a primary disorder, in an amount effective to prevent said secondary disorder, an agent or agents that sequesters AR-NOX, in a pharmaceutically acceptable carrier.

5.9. Pharmaceutical Formulations

Agents that interact with AR-NOX identified by the methods listed supra may be formulated into pharmaceutical preparations for administration to mammals for prevention or treatment of disorders in which oxidative species have been implicated. In a preferred embodiment, the mammal is a human.

Compositions comprising a compound of the invention formulated in a compatible pharmaceutical carrier may be prepared, packaged, and labeled for treatment.

If the complex is water-soluble, then it may be formulated in an appropriate buffer, for example, phosphate buffered saline or other physiologically compatible solutions. Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, rectal administration or, in the case of tumors, directly injected into a solid tumor.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g. almond oil, oily esters, or fractionated vegetable oils); and preservatives (e.g. methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

The compounds may also be formulated as a topical application, such as a cream or lotion.

In addition to the formulations described previously, the compounds may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers therapeutically or prophylactically effective amounts of the compositions in pharmaceutically acceptable form. The composition in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of compositions by a clinician or by the patient.

6. EXAMPLE a Multifunctional Ubiquinol Oxidase of the External Cell Surface and Sera

6.1. Materials and Methods 6.1.1. Measurement of Oxidation of Ubiquinol and of NADH Oxidation Ubiquinol oxidation was estimated based on increase in absorbance at 410 nm for ubiquinone (FIG. 1). NADH oxidation was determined from the decrease in $A_{340}$ measured spectrophotometrically as described (Brightman et al., 1992, Biochim. Biophys. Acta 1105:109–117).

6.1.2. Superoxide generation by Cells and Response to UV

The generation of superoxide radical was determined by assaying the rate of superoxide dismutase (SOD)-inhibitable cytochrome c reduction (Mayo and Curnette, 1990, Meth Enzymol. 186:567–575 and Butler et al., 1982, J. Biol. Chem. 257:10747–10750). The cytochrome c was from horse heart mitochondria (type VI, Sigma) and was dissolved in PBSG buffer (see below) to make a solution with a concentration of 1 mg/ml. Air-saturated reaction mixtures of 100 ml cytochrome c stock solution and 50 ml of a cell suspension (suspended in PBSG buffer) to give a final concentration of ~5×10$^6$ cells/ml were added to 2 ml of PBSG buffer (138 mM NaCl, 2.7 mM KCl, 8.1 mM Na$_2$HHPO$_4$, pH 7.4 supplemented with 0.9 mM CaCl$_2$, and 7.5 mM glucose and contained in plastic cuvettes. The formation of reduced cytochrome c was measured in the presence and absence of SOD (15 mg, Sigma) or capsaicin (2.5 mM) by comparing the absorbance of the mixture at 550 nm–540 nm. Superoxide formation was stimulated by using a handheld UV light (254 nm, 200 mw/cm$^2$). The extent of cytochrome c reduction was monitored spectrophotometrically at 550 nm every ten sec with gentle mixing between readings. Data were analyzed from the slope of the change in a 550 nm–540 nm before and after UV and then again after SOD or capsaicin was added. Data were expressed as nmoles $O_2^+/10^6$ cells using a value of $S_{M550nm}=19.1\times10^3$ $M^{-1}$ cm$^{-1}$.

6.1.3. Cytochrome c Reduction by Sera and Inhibition by Ubiquinone ($Q_{10}$)

Cytochrome c reduction by sera was assayed as for cells except that the samples were not mixed in between readings. The $Q_{10}$ was added as an ethanolic solution.

Sera were obtained from the patient population of St. Elizabeth Hospital, Lafayette, Ind. and the resident population of St. Anthony's Health Care, Lafayette, Ind. Confidentiality of medical records was assured by assigning a number to each sample.

6.2. Results 6.2.1. Characteristics of NOX

Characteristics of the surface quinol oxidase (FIG. 1) are summarized in Table 2. The protein is of relatively low abundance and specific activity but sufficient to catalyze a substantial flow of electrons from cytosolic reduced pyridine nucleotide to molecular oxygen. Molecular oxygen has been shown to represent a physiological electron acceptor for the oxidase. However, under certain conditions, protein disulfides also may function as acceptors (Morré, 1994, J. of Bioenerg. and Biomemb. 26:421–433).

TABLE 2

Properties of NOX-catalyzed oxidation of ubiquinol.

| | |
|---|---|
| pH optimum | 7.0 |
| EC$_{50}$ LY181984[a] inhibition | 30 nM (competitive) |
| EC$_{50}$ capsaicin[b] inhibition | 1 nM (competitive) |
| Cyanide | Resistant |
| NOX-specific monoclonal antibodies | Inhibited |
| K$_m$ for quinol | 33 mM |
| V$_{max}$ (nmoles/min/mg pro) | 3 |
| Oxygen consumption (nmoles/min/mg/pro) | 2.5 |

[a]N-(4-methylphenylsulfonyl)-N'-(4-chlorophenyl)urea
[b]8-methyl-N-vanillyl-6-noneamide 6.2.2. In Vitro Generation of Reactive Oxygen Species Cultured cells were subjected to ultraviolet light to perturbate electron flow to show that if the orderly two electron flow to molecular oxygen or protein thiols was suitably interrupted, a one electron process producing superoxide results. Such production leads to formation of hydrogen peroxide and possibly other oxidants such as hydroxide radical. These reactive oxygen species could then be released into the environment to react with neighboring cells and circulating molecules such as low density lipoproteins (IDLs). Results indicate that based on superoxide SOD-inhibitable reduction of cytochrome c, superoxide was generated by all three cell lines tested (Table 3). The SOD-inhibitable reduction of cytochrome c is assumed to be due at least partially to the cell surface NADH oxidase based on drug responsiveness. The HeLa (human cervical carcinoma) and BT-20 (human mammary adenocarcinoma) cells contain an activity form of the ubiquinol oxidase that is drug responsive (Morré et al., 1995, Proc. Natl. Acad. Sci. U.S.A. 92:1831–1835). Among the inhibitors that are specific to the cancer activity form are putative quinone site inhibitors such as capsaicin and the antitumor sulfonylurea LY181984 (Morré et al., 1995, Proc. Natl. Acad. Sci. U.S.A. 92:1831–1835). The MCF-10A (noncancerous human mammary epithelia) cells that lack the capsaicin-responsive NADH oxidase also lack the capsaicin-responsive UV-induced generation of superoxide (Morré et al., 1995, Proc. Natl. Acad. Sci. U.S.A. 92:1831–1835).

TABLE 3

Superoxide production (reduction of cytochrome c) by cell lines in response to UV irradiation and inhibition by superoxide dismutase (SOD) and by capsaicin.

Reduction of cytochrome c as a measure of superoxide formation, nmoles/min/$10^6$ cells

| Cell line[1] | Initial | After UV[2] | | |
|---|---|---|---|---|
| | | No Addition | + SOD[3] | + Capsaicin[4] |
| HeLa S | 0.8 ± 0.16 | 4.0 ± 1.0 | 1.1 | 0.8 |
| BT-20 | 0.7 ± 0.2 | 5.1 ± 2.1 | −0.1 | −3.7 |
| MCF 10A | 1.5 ± 0.2 | 7.2 ± 0.1 | −0.7 | 7.2 |

[1] HeLa S, human cervical carcinoma; BT-20, human mammary adenocarcinoma; MCF 10A, human mammary epithelia (non-cancer).
[2] 10 minutes of 254 nm, 200 mw/$cm^2$
[3] 15 mg (Sigma)
[4] 2.5 mM added in DMSO. Rates were corrected for a DMSO blank (0.1% final concentration)

6.2.3. Evidence for AR-NOX

A partially-purified preparation of the oxidase from HeLa cells also responds to UV by generation of SOD- and capsaicin-inhibited superoxide, suggesting that the effect of UV is directly on the oxidase. It has previously been suggested that NADPH oxidase may be a source of reactive oxygen species generated by UV irradiation based on inhibition by diphenyliodinium (Gorman et al., 1997, FEBS Lett. 404:27–33).

The Inventors have identified a serum form of AR-NOX that is specific to sera from elderly subjects and low or absent from sera of younger subjects (FIG. 2). Sera contains NADH oxidase activities with properties similar if not identical to those of the NADH oxidase found at the cell surface (Morré et al., 1997, Archives Biochem. Biophys. 342:224–230). The invention contemplates the characterization and cloning of AR-NOX from the sera of aging patients. The invention further contemplates large scale isolation and purification of AR-NOX activity in the sera of subjects of advanced age in a simple and non-invasive procedure for side-by-side comparisons with sera of young adults. Such isolation and purification methods are known in the art (Chueh et al., 1997, Archives Biochem. Biophys. 342:38–47).

Based on results of Table 3, the ability of sera to reduce cytochrome c was measured. Sera of aged patients exhibited a much more dramatic rate of cytochrome c reduction than sera of young to middle-aged patients (Table 4, FIG. 3). Sex differences, if any, were negligible with sera from both male and female patients giving similar responses.

TABLE 4

Reduction of cytochrome c by sera comparing individuals aged 21–46 years and individuals aged 76–98 years and response to superoxide dismutase (SOD) and ubiquinone ($Q_{10}$)

| | nmoles/min/ml/sera | | |
|---|---|---|---|
| Patient age | No Addition | + 15 mg SOD | + 45 mg $Q_{10}$ |
| 21–46 years (n = 16) | 0.02 ± 0.1 | 0.02 ± 0.05 | — |
| 76–98 years (n = 15) | 1.5 ± 0.9 | 1.3 ± 0.8 | — |
| 83–95 years (n = 5) | 3.9 ± 1.6 | — | 2.5 ± 1.4 |

Unlike the UV-induced changes with cells (Table 3, FIG. 3), the reduction of cytochrome c by sera of aged patients occurred spontaneously (no need for UV induction) and was only partially inhibited by SOD. An interesting feature of the reduction of cytochrome c by sera of aged patients was that the activity was inhibited 36% on average by ubiquinone. The degree of inhibition by 0.1 mM ubiquinone varied from 6 to 90%.

NOX activities of cells, plasma membrane and sera (as well as the purified protein) oscillate with a period of 24 minutes. The oscillations are given by both the oxidation of NADH and by the oxidation of ubiquinol or reduced vitamin $K_1$ (Morré, 1998, Plasma Membrane Redox Systems and their Role in Biological Stress and Disease, Klewer Academic Publishers, Dordrecht, The Netherlands, pp. 121–156). The oscillations have been observed for several NADH oxidase activity forms such that the oscillations now serve in the laboratory as a diagnostic feature to identify NOX activity forms during their purification (Morré, 1998, Plasma Membrane Redox Systems and their Role in Biological Stress and Disease, Klewer Academic Publishers, Dordrecht, The Netherlands, pp. 121–156).

Sera of healthy individuals normally exhibit an NADH oxidase activity with a major period of 24 minutes (single arrows, FIG. 2A). There is, however, a second set of oscillations that conform to a period of about 26 min (double arrows, FIG. 2A). The latter oscillations are augmented in sera of aged patients (FIG. 2B). The aging-related oscillatory activity represents a unique isoform since it is resistant to inhibition by retinoic acid (10 mM) whereas the isoform with a 26 minute period in sera of healthy individuals appears to be inhibited by retinoic acid.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method of screening for agents that sequester AR-NOX, comprising:
   (a) incubating AR-NOX with a test agent for a time sufficient to allow the test agent to bind AR-NOX; and
   (b) detecting the presence of a complex comprising AR-NOX and the test agent.

2. The method of claim 1 wherein the test agent is detectably labeled by a dye, an enzyme, an isotope, a fluorescent group, or a luminescent group.

3. The method of claim 1 wherein said method further comprises incubating AR-NOX with a component that is known to interact with AR-NOX.

4. The method of claim 3 wherein said component that is known to interact with AR-NOX is ubiquinone.

5. The method of claim 1 wherein the method of screening takes place within a cell.

6. A method of screening for agents that sequester AR-NOX comprising:
   (a) incubating AR-NOX with a test agent, cytochrome c, and a substrate that generates reactive oxygen species, for a time sufficient for cytochrome c reduction; and
   (b) detecting the presence of reduced cytochrome c, in the presence or absence of the test agent, whereas the absence of reduced cytochrome c in the mixture comprising the test agent indicates that the test agent sequesters AR-NOX.

7. The method of claim 6 wherein the substrate that generates reactive oxygen species is superoxide dismutase.

8. The method of claim 6 wherein said detecting step comprises comparing spectrophotometric absorbance at about 540 nm to 550 nm in the presence of said test agent to the spectrophotometric absorbance at about 540 nm to 550 nm in the absence of said test agent.

9. A method of screening for agents that sequester AR-NOX comprising:
   (a) incubating AR-NOX with a test agent and a substrate, wherein said substrate is reduced by AR-NOX, for a time sufficient for AR-NOX to reduce said substrate; and
   (b) detecting the presence of reduced substrate in the presence or absence of the test agent, whereas the absence of reduced substrate in the mixture comprising the test agent indicates that the test agent sequesters AR-NOX.

10. The method of claim 9 wherein the substrate reduced by AR-NOX is an ascorbate radical.

11. The method of claim 10 wherein said detecting step comprises comparing spectrophotometric absorbance at about 265 nm in the presence of said test agent to the spectrophotometric absorbance at about 265 nm in the absence of said test agent.

12. The method of claim 9 wherein the substrate reduced by AR-NOX is $NAD^+$.

13. A method of screening for agents that sequester AR-NOX comprising
   (a) incubating AR-NOX with a test agent a substrate, wherein said substrate undergoes disulfide-thiol interchange in the presence of AR-NOX, for a time sufficient for AR-NOX to reduce said substrate; and
   (b) detecting the presence of disulfide-thiol interchange in the substrate in the presence or absence of the test agent, whereas the absence of disulfide-thiol interchange in the substrate in the mixture comprising the test agent indicates that the test agent sequesters AR-NOX.

* * * * *